US011066696B2

(12) United States Patent
Wittwer et al.

(10) Patent No.: US 11,066,696 B2
(45) Date of Patent: Jul. 20, 2021

(54) QUANTUM METHOD FOR FLUORESCENCE BACKGROUND REMOVAL IN DNA MELTING ANALYSIS

(71) Applicant: UNIVERSITY OF UTAH RESEARCH FOUNDATION, Salt Lake City, UT (US)

(72) Inventors: Carl T. Wittwer, Salt Lake City, UT (US); Lindsay N. Sanford, Temple, TX (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 863 days.

(21) Appl. No.: 14/914,996

(22) PCT Filed: Aug. 29, 2014

(86) PCT No.: PCT/US2014/053558
§ 371 (c)(1),
(2) Date: Feb. 26, 2016

(87) PCT Pub. No.: WO2015/031842
PCT Pub. Date: Mar. 5, 2015

(65) Prior Publication Data
US 2016/0202195 A1 Jul. 14, 2016

Related U.S. Application Data

(60) Provisional application No. 61/872,173, filed on Aug. 30, 2013.

(51) Int. Cl.
*C12Q 1/6806* (2018.01)
*G01N 21/64* (2006.01)
*C12Q 1/686* (2018.01)
*G01N 25/04* (2006.01)
*C12Q 1/6827* (2018.01)

(52) U.S. Cl.
CPC ......... *C12Q 1/6827* (2013.01); *C12Q 1/6806* (2013.01); *C12Q 1/686* (2013.01); *G01N 21/6428* (2013.01); *G01N 25/04* (2013.01); *G01N 2201/12* (2013.01)

(58) Field of Classification Search
None
See application file for complete search history.

(56) References Cited

U.S. PATENT DOCUMENTS

| 7,387,887 | B2 | 6/2008 | Wittwer et al. | |
|---|---|---|---|---|
| 7,456,281 | B2 | 11/2008 | Wittwer et al. | |
| 7,582,429 | B2 | 9/2009 | Wittwer et al. | |
| 8,068,992 | B2 * | 11/2011 | Palais | C12Q 1/6816 |
| | | | | 702/19 |
| 8,296,074 | B2 | 10/2012 | Palais et al. | |
| 8,399,189 | B2 | 3/2013 | Wittwer et al. | |
| 2003/0157538 | A1 | 8/2003 | Krull et al. | |
| 2007/0026421 | A1 * | 2/2007 | Sundberg | B01L 3/5027 |
| | | | | 435/6.12 |
| 2009/0117553 | A1 | 5/2009 | Wittwer et al. | |
| 2011/0112772 | A1 * | 5/2011 | Yost | G01J 3/28 |
| | | | | 702/24 |
| 2012/0116686 | A1 * | 5/2012 | Palais | C12Q 1/6816 |
| | | | | 702/19 |
| 2014/0162244 | A1 * | 6/2014 | Bau | C12Q 1/703 |
| | | | | 435/5 |
| 2014/0273181 | A1 | 9/2014 | Abbott et al. | |

FOREIGN PATENT DOCUMENTS

| CN | 102428459 | 4/2012 |
|---|---|---|
| KR | 20110037379 | 4/2011 |
| WO | 2009156916 | 12/2009 |
| WO | 2014058919 | 4/2014 |
| WO | 2015031842 | 3/2015 |

OTHER PUBLICATIONS

Palais et al., "Mathematical Algorithms for High-Resolution DNA Melting Analysis." Methods in Enzymology, Computer Methods Part A [online], vol. 454, 2009 [Retrieved on Oct. 31, 2014], pp. 323-343.
Sanford et al., "Quantum Method for Fluorescence Background Removal in DNA Melting Analysis." Analytical Chemistry [online], Epub Sep. 26, 2013, vol. 85, Issue 20 [Retrieved on Oct. 31, 2014], pp. 9907-9915.
U.S. International Search Authority, International Search Report and Written Opinion, Completed Oct. 31, 2014, PCT/US2014/053558.
Sanford et al. "Monitoring Temperature by Fluorescence During PCR and Melting Analysis", The University of Utah, Nov. 5, 2012, XP055476665, 1 page.
Sanford et al. "Monitoring Temperature with Fluorescence During Real-Time PCR and Melting Analysis" Analytical Biochemistry, vol. 434, No. 1, Mar. 1, 2013, pp. 26-33.

(Continued)

*Primary Examiner* — Lori A. Clow
(74) *Attorney, Agent, or Firm* — Workman Nydegger

(57) ABSTRACT

A method of background removal from melting curves generated using a fluorescent dye is provided for analyzing a melting profile of a nucleic acid sample. The method comprises measuring the fluorescence of the nucleic acid sample as a function of temperature to produce a raw melting curve having a melting transition, the nucleic acid sample comprising a nucleic acid and a molecule that binds the nucleic acid to form a fluorescently detectable complex, the raw melting curve comprising a background fluorescence signal and a nucleic acid sample signal; and separating the background signal from the nucleic acid sample signal by use of a quantum algorithm to generate a corrected melting curve, the corrected melting curve comprising the nucleic acid sample signal.

6 Claims, 18 Drawing Sheets
Specification includes a Sequence Listing.

(56) References Cited

OTHER PUBLICATIONS

Supplemental European Search Report for EP14838978 dated Feb. 8, 2017.
Abrams, et al. "Comprehensive Detection of Single Base Changes in Human Genomic DNA Using Denaturing Gradient Gel Electrophoresis and a GC Clamp," Genomics, 1990, vol. 7, No. 4, pp. 463-475.
Crockett et al., "Fluorescein-Labeled Oligonucleotides for Real-Time PCR: Using the Inherent Quenching of Deoxyguanosine Nucleotides," Analytical Biochemistry 2001, 290; 89-97.
Dwight et al., "uMELT: Prediction of high-resolution melting curves and dynamic melting profiles of PCR products in a rich web application," Bioinformatics, 27(7), 2011, pp. 1019-1020.
Erali et al., "SNP Genotyping by Unlabeled Probe Melting Analysis," Methods Mol. Biol. 2008, 429: 199-206.
Erali et al., "High Resolution Melting Analysis for Gene Scanning," Methods. 2010, 50: 250-261.
Guilbault, "Practical Fluorescence," 2nd Edition; Marcel Dekker Inc., NY 1990, Chapter 2: Instrumentation by Fluorescence 19 pages.
Gundry et al., "Amplicon Melting Analysis with Labeled Primers: A Closed-Tube Method for Differentiating Homzygotes and Heterozygotes," Clincial Chemistry, 49:3 (2003), pp. 396-406.
Lay et al., "Real-time fluorescence genotyping of factor V Leiden during rapid-cycle PCR," Clinical Chemistry, 1997, 43:12, pp. 2262-2267.
Lemoine et al., "Simultaneous Concentration and Velocity Measurement Using Combined Laser-Induced Fluorescence and Laser Doppler Velocimetry: Application to Turbulent Transport," Experiments in Fluids, 1996; 20:319-327.
Lemoine et al., "Simultaneous Temperature and 2D Velocity Measurements in a Turbulent Heated Jet Using Combined Laser-Induced Fluorescence and LDA," Experiments in Fluids. 1999; 26:315-323.
Liew et al., "Genotyping of Human Platelet Antigens 1-6 and 15 by High-Resolution Amplicon Melting and Conventional Hybridization Probes," J. Mol. Diag. 2006, 8, p. 97-104.
Liew et al., "Genotyping of Single-Nucleotide Polymorphisms by High-Resolution Melting of Small Amplicons," Clin. Chem. 2004, 50:7, pp. 1156-1164.
Mergny et al., "Analysis of Thermal Melting Curves," Oligonucleotides. 2003; 13:515-537.
Montgomery et al., "High-Resolution DNA Melting Analysis in Clinical Research and Diagnostics," Expert Rev. Mol. Diagn. 2010, 10, 219-240.
Montgomery et al., "Simultaneous Mutation Scanning and Genotyping by High-Resolution DNA Melting Analysis," Nature Protocols. 2007, 2:59-66.
Nataraj et al., "Sing-Strand Conformation Polymorphism and Heteroduplex Analysis for Gel-Based Mutation Detection," Electrophoresis, 1999 vol. 20, pp. 1177-1185.
Orita et al., "Detection of Polymorphisms of Human DNA by Gel Electrophoresis as Sing-Strand Conformation Polymorphisms," Proc. Natl. Acad. Sci. USA; 1989 vol. 86, pp. 2766-2770.
Reed et al., "High-Resolution DNA Melting Analysis for Simple and Efficient Molecular Diagnostics," Pharmacogenomics. 2007, 8:597-608.
Ross et al., "Temperature Measurement in Microfluidic Systems Using a Temperature Dependent Fluorescent Dye," Analytical Chemistry 2001; 73:4117-4123.
Seipp et al., "Quadruplex Genotyping of F5, F2, and MTHFR Variants in a Single Closed Tube by High-Resolution Amplicon Melting," clin. Chem. 2008, 54:108-115.
Taylor et al., "Enzymatic Methods for Mutation Scanning," Genetic Analyais, 1999 14:181-6.
Walker, "A Fluorescence Technique for Measurement of Concentration in Mixing Liquids," Journal of Physics E: Scientific Instruments, 1987; 20:217-224.
Wartell, et al., "Detecting Single Base Substitutions, Mismatches and Bulges in DNA by Temperature Gardient Gel Electrophoresis and Related Methods," Journal of Chromatography A, 1998, vol. 806, pp. 169-185.
Xiao, et al., "Denaturing High-Performance Liquid Chromatography: A Review," Human Mutation, 2001, vol. 17, pp. 439-474.
Zhou et al., "Closed-Tube Genotyping with Unlabeled Oligonucleotide Probes and a Saturating DNA Dye," Clin. Chem. 2004, 50:1328-35.
Zhou et al., "High-Resolution Melting Analysis for Simultaneous Mutation Scanning and Genotyping in Solution," Clin. Chem. 2005, 51, pp. 1770-1777.
Zhou et al., "Snapback Primer Genotyping with Saturating DNA Dye and Melting Analysis," Clinical Chemistry, 2008, 54:10, pp. 1648-1656.

* cited by examiner

SEQUENCE LISTING

<160> NUMBER OF SEQ ID NOS: 15

<210> SEQ ID NO 1
<211> LENGTH: 14
<212> TYPE: DNA
<213> ORGANISM: Artificial Sequence
<220> FEATURE:
<223> OTHER INFORMATION: synthetic hairpin with 6 bp loop

<400> SEQUENCE: 1
gcagcccccc ctgc     14

<210> SEQ ID NO 2
<211> LENGTH: 18
<212> TYPE: DNA
<213> ORGANISM: Artificial Sequence
<220> FEATURE:
<223> OTHER INFORMATION: synthetic hairpin with 6 bp loop

<400> SEQUENCE: 2

```
tggcagcccc ccctgcca                                                        18

<210> SEQ ID NO 3
<211> LENGTH: 22
<212> TYPE: DNA
<213> ORGANISM: Artificial Sequence
<220> FEATURE:
<223> OTHER INFORMATION: synthetic hairpin with 6 bp loop

<400> SEQUENCE: 3
tatggcagcc ccccctgcca ta                                                   22

<210> SEQ ID NO 4
<211> LENGTH: 30
<212> TYPE: DNA
<213> ORGANISM: Artificial Sequence
<220> FEATURE:
<223> OTHER INFORMATION: synthetic hairpin with 6 bp loop

<400> SEQUENCE: 4
cgtatatggc agccccccct gccatatcag                                           30

<210> SEQ ID NO 5
<211> LENGTH: 44
<212> TYPE: DNA
<213> ORGANISM: Artificial Sequence
<220> FEATURE:
<223> OTHER INFORMATION: synthetic DNA used to mimic asymmetric PCR

<400> SEQUENCE: 5
tggcaagagg taactcaatc actagcttaa agcactctat ccaa                           44

<210> SEQ ID NO 6
<211> LENGTH: 44
<212> TYPE: DNA
<213> ORGANISM: Artificial Sequence
<220> FEATURE:
<223> OTHER INFORMATION: synthetic DNA used to mimic asymmetric PCR

<400> SEQUENCE: 6
ttggatagag tgctttaagc tagtgattga gttacctctt gcca                           44

<210> SEQ ID NO 7
<211> LENGTH: 13
<212> TYPE: DNA
<213> ORGANISM: Artificial Sequence
<220> FEATURE:
<223> OTHER INFORMATION: Probe for detection of synthetic DNA used to
      mimic asymmetric PCR

<400> SEQUENCE: 7
caatcactag ctt                                                             13

<210> SEQ ID NO 8
<211> LENGTH: 50
<212> TYPE: DNA
<213> ORGANISM: Artificial Sequence
<220> FEATURE:
<223> OTHER INFORMATION: synthetic DNA used to mimic PCR

<400> SEQUENCE: 8
tctgctctgc ggctttctgt ttcaggaatc caagagcttt tactgcttcg                     50

<210> SEQ ID NO 9
<211> LENGTH: 28
```

```
<212> TYPE: DNA
<213> ORGANISM: Homo sapiens
<220> FEATURE:
<221> NAME/KEY: misc_feature
<222> LOCATION: (1)..(2)
<223> OTHER INFORMATION: mismatch to prevent extension
<220> FEATURE:
<221> NAME/KEY: misc_binding
<222> LOCATION: (3)..(8)
<223> OTHER INFORMATION: Snapback probe element

<400> SEQUENCE: 9
cctagtgatg gcaagaggta actcaatc                                       28

<210> SEQ ID NO 10
<211> LENGTH: 21
<212> TYPE: DNA
<213> ORGANISM: Homo sapiens

<400> SEQUENCE: 10
ttggatagag tgctttaagc t                                              21

<210> SEQ ID NO 11
<211> LENGTH: 21
<212> TYPE: DNA
<213> ORGANISM: Homo sapiens

<400> SEQUENCE: 11
tggggaagag cagagatata c                                              21

<210> SEQ ID NO 12
<211> LENGTH: 15
<212> TYPE: DNA
<213> ORGANISM: Homo sapiens

<400> SEQUENCE: 12
tgggtgctcc acctg                                                     15

<210> SEQ ID NO 13
<211> LENGTH: 16
<212> TYPE: DNA
<213> ORGANISM: Homo sapiens

<400> SEQUENCE: 13
tgggctacgt ggatga                                                    16

<210> SEQ ID NO 14
<211> LENGTH: 17
<212> TYPE: DNA
<213> ORGANISM: Homo sapiens

<400> SEQUENCE: 14
aaacccatgg agttcgg                                                   17

<210> SEQ ID NO 15
<211> LENGTH: 27
<212> TYPE: DNA
<213> ORGANISM: Homo sapiens
<220> FEATURE:
<221> NAME/KEY: misc_feature
<222> LOCATION: (26)..(27)
<223> OTHER INFORMATION: mis-match to prevent extension

<400> SEQUENCE: 15
gctgttcgtg ttctatgatc atgaggc                                        27
```

QUANTUM METHOD FOR FLUORESCENCE BACKGROUND REMOVAL IN DNA MELTING ANALYSIS

CROSS-REFERENCE TO RELATED APPLICATIONS

This application claims priority to and the benefit of PCT Application No. PCT/US2014/053558, filed Aug. 29, 2014, entitled "A QUANTUM METHOD FOR FLUORESCENCE BACKGROUND REMOVAL IN DNA MELTING ANALYSIS", which claims the benefit of and priority to U.S. Provisional Application No. 61/872,173, filed Aug. 30, 2013, entitled "QUANTUM METHOD FOR FLUORESCENCE BACKGROUND REMOVAL IN DNA MELTING ANALYSIS". All the aforementioned applications are incorporated by reference herein in their entirety.

BACKGROUND OF THE INVENTION

Helicity is a measure of the fraction of nucleic acid in double-stranded form. Classical absorbance measurements of hyperchromicity using measurements at 260 nm use simple baseline extrapolation and normalization to generate melting curves that closely match helicity predictions. Absorbance melting curves are the "gold standard" for DNA helicity, but they require relatively large quantities of DNA (on the order of µg) and slow melting rates of 0.1-1.0° C./min. Fluorescent methods for DNA melting have become popular recently, in part because they can use significantly smaller quantities of nucleic acid and can be performed on PCR mixtures, often in the same real-time PCR instruments. Melting curves generated by fluorescence monitoring also have the advantage that they can be generated at rates 60-fold faster than absorbance measurements. While absorbance methods are considered to be the gold standard, fluorescent melting curves have gained widespread use. However, melting curves generated using fluorescence methods are influenced by the presence of the dye.

Methods for analyzing DNA sequence variation can be divided into two general categories: 1) genotyping for known sequence variants and 2) scanning for unknown variants. There are many methods for genotyping known sequence variants, and single step, homogeneous, closed tube methods that use fluorescent probes are available (Lay M J, et al., Clin. Chem 1997; 43:2262-7). In contrast, most scanning techniques for unknown variants require gel electrophoresis or column separation after PCR. These include single strand conformation polymorphism (Orita O, et al., Proc Natl Acad Sci USA 1989; 86:2766-70), heteroduplex migration (Nataraj A J, et al., Electrophoresis 1999; 20:1177-85), denaturing gradient gel electrophoresis (Abrams E S, et al., Genomics 1990; 7:463-75), temperature gradient gel electrophoresis (Wartell R M, et al., J Chromatogr A 1998; 806:169-85), enzyme or chemical cleavage methods (Taylor G R, et al., Genet Anal 1999; 14:181-6), as well as DNA sequencing. Identifying new mutations by sequencing also requires multiple steps after PCR, namely cycle sequencing and gel electrophoresis. Denaturing high-performance liquid chromatography (Xiao W, et al., Hum Mutat 2001; 17:439-74) involves injecting the PCR product into a column. Massively parallel sequencing requires multiple steps and expensive instrumentation, and the turnaround time is very long compared to a one or two minute melting curve without any extra processing after PCR.

Single nucleotide polymorphisms (SNPs) are by far the most common genetic variations observed in man and other species. In these polymorphisms, only a single base varies between individuals. The alteration may cause an amino acid change in a protein, alter rates of transcription, affect mRNA spicing, or have no apparent effect on cellular processes. Sometimes when the change is silent (e.g., when the amino acid it codes for does not change), SNP genotyping may still be valuable if the alteration is linked to (associated with) a unique phenotype caused by another genetic alteration.

There are many methods for genotyping SNPs. Most use PCR or other amplification techniques to amplify the template of interest. Contemporaneous or subsequent analytical techniques may be employed, including gel electrophoresis, mass spectrometry, and fluorescence. Fluorescence techniques that are homogeneous and do not require the addition of reagents after commencement of amplification or physical sampling of the reactions for analysis are attractive. Exemplary homogeneous techniques use oligonucleotide primers to locate the region of interest and fluorescent labels or dyes for signal generation. Various PCR-based methods are completely closed-tubed, using a thermostable enzyme that is stable to DNA denaturation temperature, so that after heating begins, no additions are necessary.

Several closed-tube, homogeneous, fluorescent PCR methods are available to genotype SNPs. These include systems that use FRET oligonucleotide probes with two interacting chromophores (adjacent hybridization probes, TaqMan™ probes, Molecular Beacons, Scorpions), single oligonucleotide probes with only one fluorophore (G-quenching probes, Crockett, A. O. and C. T. Wittwer, Anal. Biochem. 2001; 290:89-97 and SimpleProbes, BioFire Diagnostics), and techniques that use a dsDNA dye instead of covalent, fluorescently-labeled oligonucleotide probes.

PCR methods that monitor DNA melting with dsDNA fluorescent dyes have become popular in conjunction with real-time PCR. Because PCR produces enough DNA for fluorescent melting analysis, both amplification and analysis can be performed in the same tube, providing a homogeneous, closed-tube system that requires no processing or separation steps. dsDNA dyes are commonly used to identify products by their melting temperature, or Tm.

The power of DNA melting analysis depends on its resolution. High-resolution melting analysis for gene scanning relies primarily on the shape of the melting transition of the PCR products. In many cases, high-resolution analysis of the melting transition also allows genotyping without probes. Even greater specificity for variant discrimination over a smaller region can be obtained by using labeled or unlabeled probes. Specific genotypes are inferred by correlating sequence alterations under the probe to changes in the probe Tm. With the recent advances with dyes and instrumentation, high-resolution gene scanning and genotyping with unlabeled probes can optionally be done simultaneously in the same reaction (U.S. Pat. No. 7,582,429, herein incorporated by reference in its entirety). Both PCR product and probe melting transitions may be observed in the presence of a saturating DNA dye. In addition to screening for any sequence variant between the primers in the PCR product, common polymorphisms and mutations can be genotyped. Furthermore, unbiased, hierarchal clustering can accurately group the melting curves into genotypes (U.S. Pat. No. 8,296,074, herein incorporated by reference in its entirety). One, two, or even more unlabeled probes can be used in a single PCR.

In simultaneous genotyping and scanning, product melting analysis detects sequence variants anywhere between two primers, while probe melting analysis identifies variants under the probe. If a sequence variant is between the primers and under a probe, both the presence of a variant and its genotype are obtained. If product melting indicates a variant but the probe does not, then the variation likely occurs between the primers but not under the probe, and further analysis for genotyping may be necessary. Probes can be placed at sites of common sequence variation so that in most cases, if product scanning is positive, the probes will identify the sequence variants, greatly reducing the need for sequencing. With one probe, the genotype of an SNP can be established by both PCR product and probe melting. With two probes, two separate regions of the sequence can be interrogated for genotype and the rest of the PCR product scanned for rare sequence variants. Multiple probes can be used if they differ in melting temperature and if each allele presents a unique pattern of probe and/or product melting.

Simultaneous genotyping and scanning, as well as other genotyping techniques that employ melting analysis have been promising areas of research. However, the melting curve analysis prior to high-resolution capabilities provided a lack of specificity and accuracy. With the advent of high-resolution melting curve analysis, background fluorescence noise can interfere with the use of melting curves to accurately genotype SNPs, detect sequence variations, and detect mutations. Depending on the amplicon, previous background fluorescence removal techniques have led to some erroneous calls. By example, the baseline technique uses linear extrapolation as a method for normalizing melting curves and removing background fluorescence. This technique works well with labeled probes. However, this and other previous normalization techniques have not worked as well with unlabeled probes (Zhou L, Myers A N, Vandersteen J G, Wang L, Wittwer C T. Closed-Tube Genotyping with Unlabeled Oligonucleotide Probes and a Saturating DNA Dye. Clin Chem. 2004; 50:1328-35), multiplex small amplicon melting (Liew M, Nelson L, Margraf R, Mitchell S, Erali M, Mao R, Lyon E, Wittwer C T. Genotyping of human platelet antigens 1-6 and 15 by high-resolution amplicon melting and conventional hybridization probes. J Mol Diag, 2006; 8:97-104), and combined amplicon and unlabeled probe melting (Zhou L, Wang L, Palais R, Pryor R, Wittwer C T). High-resolution melting analysis for simultaneous mutation scanning and genotyping in solution. Clin Chem 2005; 51:1770-7, hereby incorporated by reference), nor do they work as well for small amplicons. At least in part, this is because unlabeled probe and small amplicon melting methods often require background subtraction at lower temperatures (40-80° C.) than is usual for standard amplicon melting at 80-95° C. At these lower temperatures, the low temperature baseline is not linear, but instead it is a curve with rapidly increasing fluorescence at low temperatures. When linear extrapolation is used, the lines can intersect before the melting transition is complete, and when this occurs the previous techniques do not provide the most accurate means for melting curve analysis, in part due to their mathematical reliance on absolute fluorescence.

Exponential methods have provided significant advantages over the baseline method (U.S. Pat. No. 8,068,992, herein incorporated by reference). However, exponential methods often result in low temperature distortions that could lead to inaccurate calls. It would be desirable to have a system and method that more accurately represents helicity. It would be advantageous for such a system and method to genotype SNPs, detect sequence variations, and/or detect mutations with high accuracy in double stranded nucleic acids through use of high resolution melting profile techniques. It would be further advantageous if the background fluorescence could be automatically and accurately separated from a double-stranded nucleic acid sample melting profile. It would be a further advantage if the system and method performed accurate melting curve analysis for small and large amplicons, as well as with unlabeled probes.

SUMMARY OF THE INVENTION

The present disclosure relates to a novel method of background removal from melting curves generated using a fluorescent dye. In one embodiment, a method is provided for analyzing a melting profile of a nucleic acid sample, comprising measuring the fluorescence of the nucleic acid sample as a function of temperature to produce a raw melting curve having a melting transition, the nucleic acid sample comprising a nucleic acid and a molecule that binds the nucleic acid to form a fluorescently detectable complex, the raw melting curve comprising a background fluorescence signal and a nucleic acid sample signal; and separating the background signal from the nucleic acid sample signal by use of a quantum algorithm to generate a corrected melting curve, the corrected melting curve comprising the nucleic acid sample signal.

Illustratively, the quantum method may include a separating step that includes rescaling an original x-axis and an original y-axis from the raw melting curve to:

$x = (1/T - 1/T_{REF})$ (° K) and $y = \ln(I/I_{REF})$ wherein $T_{ref}$ is a reference temperature and $I_{ref}$ is a reference fluorescence intensity of the molecule at the reference temperature. It is understood that the separating step may further include calculating a first line H(T), calculated before the melting transition, and a second line L(T), calculated after the melting transition. The separating step may also include rescaling back to the original x-axis and the original y-axis. Optionally, the method may comprise the step of proportionally calculating the melting curve.

In another illustrative embodiment a system for analyzing a nucleic acid sample is provided, the system comprising a heating system for heating a fluorescently detectable complex while monitoring its fluorescence, the complex comprising a nucleic acid and a fluorescent molecule indicative of double-stranded nucleic acids, the system being adapted to measure and to record sample temperature and sample fluorescence to determine sample fluorescence as a function of sample temperature to produce a melting profile, the melting profile comprising background fluorescence signal and sample fluorescence signal; a central processing unit (CPU) for performing computer executable instructions; and a memory storage device for storing computer executable instructions that when executed by the CPU cause the CPU to perform a process for analyzing the nucleic acid, wherein the process includes: separating a background fluorescence signal from the melting profile by means of a quantum algorithm to generate a corrected melting curve, the corrected melting curve comprising a sample signal.

Additional features of the present invention will become apparent to those skilled in the art upon consideration of the following detailed description of preferred embodiments exemplifying the best mode of carrying out the invention as presently perceived.

BRIEF DESCRIPTION OF THE FIGURES

FIG. 2A shows raw experimental data (black), while FIG. 2B shows the same data as transformed with the Y-axis=ln($I/I_{REF}$) and the X-axis=$1/T_{REF}$−1/T in ° K (black). When inverse temperature values are calculated and subtracted, decimal values on the order of $10^{-5}$ are produced, so FIG. 2B is scaled accordingly. The upper (dark grey) and lower (light grey) linear-fits correspond to the fluorescence of initial (100% helicity) and final (0% helicity) states. Equations were y=−4422.7x+0.0004 for H(T) and y=−3272.6x−1.475 for L(T). The data are then re-plotted in FIG. 2C on the original fluorescence and temperature (° C.) axes. The final melting curve (FIG. 2D) is calculated from FIG. 2C using the equation M(T)=F(T)−L(T)/H(T)−L(T), to normalize between 0-100%.

FIG. 4A shows results for an 8 bp stem hairpin, while FIG. 4B shows results for a 13 base unlabeled probe with a 1:10 strand ratio. The baseline method was used for background removal of the absorbance data (black). Fluorescent melting curve data were analyzed using the quantum (light grey) or exponential (dark grey) methods.

FIG. 5A shows results for a 4 bp stem, FIG. 5B shows results for a 6 bp stem, and FIG. 5C shows results for a 12 bp stem, with results for an 8 bp stem shown in FIG. 4A. Fluorescence data are displayed as negative-derivative plots after analysis using the quantum (light grey) or exponential (dark grey) fluorescence methods and compared to absorbance data (black) analyzed with the baseline method.

FIGS. 13A, 13C, and 13E show melting data plotted according to Equation 3, with reversed use of reference values for ease of visualization, while FIGS. 13B, 13D, and 13F show corrected melting curves. FIGS. 13C-13D show offsets of 500 fluorescence units added to the original data, while FIGS. 13E-13F show 750 fluorescence units added to the original data.

DETAILED DESCRIPTION

Figure 1A:
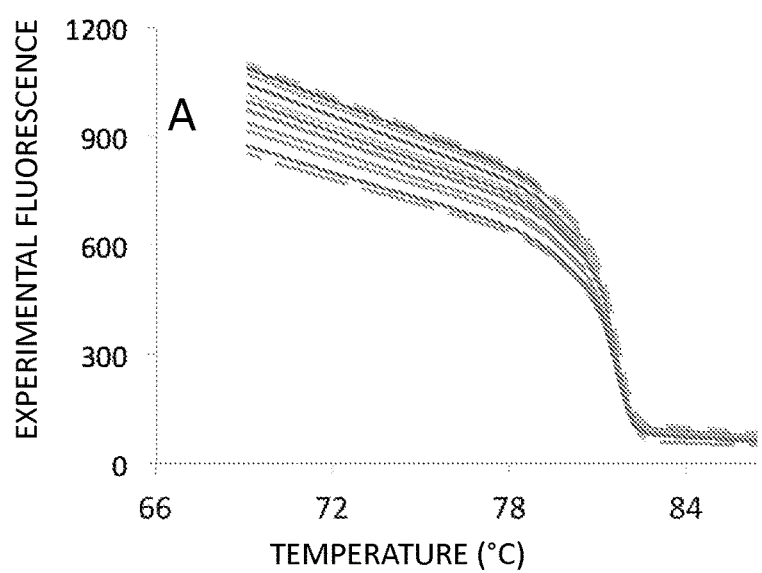
FIGS. 1A-1B show differing states of normalization and background removal, including (FIG. 1A) experimental data and (FIG. 1B) experimental data normalized between 0-100% (short dashed/long dashed) and the predicted melting transition (black). The predicted melting curve has been overlaid to the normalized experimental data to better show shape differences.

As used herein, the terms "a," "an," and "the" are defined to mean one or more and include the plural unless the context is inappropriate. Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The word "or" as used herein means any one member of a particular list and also includes any combination of members of that list.

By "sample" is meant an animal; a tissue or organ from an animal; a cell (either within a subject, taken directly from a subject, or a cell maintained in culture or from a cultured cell line); a cell lysate (or lysate fraction) or cell extract; a solution containing one or more molecules derived from a cell, cellular material, or viral material (e.g. a polypeptide or nucleic acid); or a solution containing a non-naturally occurring nucleic acid, which is assayed as described herein. A sample may also be any body fluid or excretion (for example, but not limited to, blood, urine, stool, saliva, tears, bile) that contains cells, cell components, or nucleic acids.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof By "probe," "primer," or "oligonucleotide" is meant a single-stranded DNA or RNA molecule of defined sequence that can base-pair to a second DNA or RNA molecule that contains a complementary sequence (the "target"). The stability of the resulting hybrid depends upon the length, GC content, and the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes, primers, and oligonucleotides may be detectably-labeled, either radioactively, fluorescently, or non-radioactively, by methods well-known to those skilled in the art. dsDNA binding dyes (dyes that fluoresce more strongly when bound to double-stranded DNA than when bound to single-stranded DNA or free in solution) may be used to detect dsDNA. It is understood that a "primer" is specifically configured to be extended by a polymerase, whereas a "probe" or "oligonucleotide" may or may not be so configured.

By "specifically hybridizes" is meant that a probe, primer, or oligonucleotide recognizes and physically interacts (that is, base-pairs) with a substantially complementary nucleic acid (for example, a sample nucleic acid) under high stringency conditions, and does not substantially base pair with other nucleic acids.

By "high stringency conditions" is meant conditions that allow hybridization comparable with that resulting from the use of a DNA probe of at least 40 nucleotides in length, in a buffer containing 0.5 M NaHPO4, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well known by those skilled in the art of molecular biology.

By "helicity" is meant the fraction of DNA that is double-stranded form. Thus, by cooling a nucleic acid sample thereby allowing for hybridization increases helicity, while heating a nucleic acid sample thereby melting some or all of the double-stranded nucleic acids to single-stranded nucleic acids reduces helicity.

By "fluorescent dye", "fluorescent entity", "fluorescent molecule indicative of double-stranded nucleic acids", or "molecule that binds the nucleic acid to form a fluorescently detectable complex" and similar terms refer to any molecule, component, chemical, compound, dye, reagent and/or other fluorescent material that is capable of demonstrating, suggesting, or otherwise revealing an approximate quantity of double-stranded nucleic acid in the reaction mixture. One illustrative example is a dsDNA binding dye. Such an indicator may also illustratively include a nucleic acid, protein, probe, and/or other molecule with one or more bound, tethered, conjugated, and/or otherwise associated fluorescent indicators of double-stranded nucleic acids, such as dyes, molecules, moieties, units, and so forth.

While PCR is the amplification method used in the examples herein, it is understood that any amplification method may be suitable. Such suitable procedures include polymerase chain reaction (PCR); strand displacement amplification (SDA); nucleic acid sequence-based amplification (NASBA); cascade rolling circle amplification (CRCA), loop-mediated isothermal amplification of DNA (LAMP); isothermal and chimeric primer-initiated amplification of nucleic acids (ICAN); target based-helicase dependent amplification (HDA); transcription-mediated amplification (TMA), and the like. Therefore, when the term PCR is used, it should be understood to include other alternative amplification methods. For amplification methods without discrete cycles, additional reaction time may be used where additional PCR cycles are added in the embodiments described herein. It is understood that protocols may need to be adjusted accordingly. It is also understood that the methods described herein may use nucleic acids obtained from other sources, including naturally occurring and synthetic nucleic acids.

The popularity of high-resolution DNA melting analysis has grown steadily since its introduction in 2003. Robust, simple, and conducted in a closed environment to limit contamination, it is used in research and clinical applications for genotyping (see, e.g. Liew, M.; Pryor, R.; Palais, R.; Meadows, C.; Erali, M.; Lyon, E.; Wittwer, C. Clin. Chem. 2004, 50, 1156-1164, and Erali, M.; Palais, R.; Wittwer, C. Methods Mol Biol. 2008, 429, 199-206), variant scanning (see, e.g. Gundry, C.; Vandersteen, J; Reed, G.; Pryor, J.; Chen, J.; Wittwer, C. Clin. Chem. 2003, 49, 396-406 and Erali, M.; Wittwer, C. Methods. 2010, 50, 250-261), and simultaneous genotyping and mutation scanning (see, e.g. Zhou, L.; Wang, L.; Palais, R.; Pryor, R.; Wittwer, C. Clin. Chem. 2005, 51, 1770-1777 and Montgomery, J.; Wittwer, C.; Palais, R.; Zhou, L. Nature Protocols. 2007, 2, 59-66). Obtaining quality high-resolution melting curves depends on a number of factors including PCR specificity, the fluorescent dye, instrumentation, and the algorithm used for background removal. The ability to extricate relevant information from experimental melting data can be quite important, as small differences in melting curve shape can suggest variants. Previously reported methods of background removal include extrapolation of linear baselines (commonly used for melting curves measured by absorbance) and exponential methods. See U.S. Pat. No. 8,068,992, herein incorporated by reference in its entirety. While these methods are generally successful for analyzing melting curves, in some high-resolution applications it becomes difficult to separate relevant signal from artifacts of the background removal algorithm. This most often occurs in low temperature applications, particularly those using unlabeled probes, snapback primers, or multiple small amplicons.

Illustrative fluorescent DNA melting curves are generated by tracking changes in fluorescence across temperature. In one illustrative embodiment, "saturating" dyes (those dyes that allow for heteroduplex detection, see U.S. Pat. Nos. 7,582,429 and 7,456,281, herein incorporated by reference in their entireties) are added to the PCR mixture, and fluoresce strongly in the presence of double-stranded DNA. As the mixture is heated, the double strands dissociate, resulting in a decrease in fluorescence. By continuously monitoring changes in fluorescence across temperature, fluorescent melting curves are acquired. The melting temperature ($T_m$) is the point at which half of the DNA duplex has dissociated, and is characteristic of GC content, length and sequence. The $T_m$ of the DNA duplex is evident when melting curve data are displayed on a negative-derivative plot. For accurate $T_m$ calculations, it is desirable that background signal be removed from experimental melting data, illustratively prior to normalization. Furthermore, the shape of the entire melting transition can play a key role in sequence matching, genotyping, and mutation scanning, particularly in the presence of heteroduplexes (see Montgomery, J.; Sanford, L.; Wittwer, C. Expert Rev Mol Diagn. 2010, 10, 219-240). Poor background removal can result in distorted melting curves and even introduce artifacts that can be interpreted as unique alleles, which could lead to incorrect classification. While saturating dyes are used in the examples herein, it is understood that other dsDNA binding dyes may be suitable, and other fluorescent detection systems, such as covalently fluorescently labeled nucleic acids, as are known in the art, may be employed.

A method of determining solution temperatures in PCR by fluorescence monitoring was recently described (see WO2014/058919, herein incorporated by reference in its entirety). Based on first principles beginning with Beer's law, this method determines average solution temperatures from fluorescence by calculating a calibration constant that relates fluorescence to temperature. This method (here referred to as the quantum method) has been extended to calculate background fluorescence in melting data, with the goal of better representing helicity and reducing or eliminating artificial low temperature domains produced by other background removal algorithms.

Figure 1B:
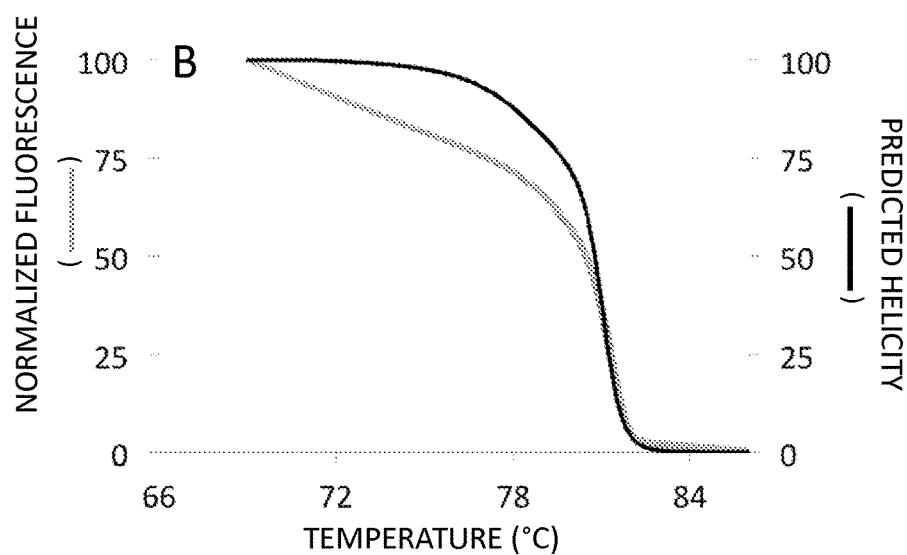

In an illustrative method, background signal is removed prior to determining helicity from experimental melting data. FIGS. 1A-1B demonstrate an illustrative background removal process when analyzing fluorescent melting curves. Raw melting data (FIG. 1A) show poor curve clustering, with a steep slope at low temperatures and a tail having a non-zero slope at high temperatures. The results of applying simple normalization (data scaled from 0-100%) compared to predicted helicity are shown in FIG. 1B (more information on normalization may be found in U.S. Pat. No. 7,582,429, already incorporated by reference). With normalization, signal levels are forced to zero at high temperatures and curve clustering is improved. However, when overlaid against a predicted melting transition generated using uMelt$^{SM}$ (a web-based software application designed to predict high-resolution DNA melting curves of PCR products, see Dwight, Z.; Palais, R.; Wittwer, C. Bioinformatics. 2011, 27, 1019-1020) the difference between the normalized and predicted melting curves is apparent. The predicted melting curve using uMelt$^{SM}$ exhibits a zero slope at low temperatures, with signal levels reaching zero at high temperatures (when the DNA is completely denatured). These comparisons demonstrate that simple normalization does not appear to completely remove background signal in fluorescent melting curves, and they demonstrate that robust background removal algorithms are necessary if one desires to match experimental data to helicity predictions.

Quantum Method

One illustrative method is described to eliminate the temperature effect on fluorescence and remove artificial melting domains that occur with other background removal methods. This "quantum method" is derived from Beer's law (see Lemoine, F.; Wolff, M.; Lebouche, M. Exp. Fluids. 1996, 20, 319-327 and Lemoine, F.; Antoine, Y.; Wolff, M.; Lebouche, M. Exp. Fluids. 1999, 26, 315-323, herein incorporated by reference), wherein the equation for temperature-dependent fluorescence intensity may be written as:

$$I = I_0 c \Phi \varepsilon \quad \text{[Equation 1]}$$

where:
I=emitted (emission) fluorescence intensity
$I_0$=excitation intensity
c=concentration of the fluorescent dye
$\Phi$=quantum efficiency of the fluorescent dye
$\varepsilon$=absorption coefficient of the fluorescent dye When the concentration of the dye is sufficiently small, the intensity of the emission will be proportional to concentration while the bulk of temperature sensitivity will lie in the fluorescence quantum yield. Equation 1 can be further expanded using fundamental principles to express the emission intensity as a function of temperature:

$$I = I_0 c e^{C/T} \quad \text{[Equation 2]}$$

where:
C=calibration constant
T=average solution temperature

While concentration may be kept constant, variations in the excitation intensity may be more difficult to control and can significantly affect the accuracy of the temperature measurement. Dividing by reference intensity and reference temperature allows for dependencies on the excitation intensity and dye concentration to be largely eliminated leading to an equation of the form:

$$\ln(I/I_{ref}) = C(1/T - 1/T_{ref}) \quad \text{[Equation 3]}$$

where:
$T_{ref}$ is a reference temperature
$I_{ref}$ is the reference fluorescence intensity of the fluorescent dye at the reference temperature.

After conversion to ° K, rather than ° C., the calibration constant, C, may be determined as the slope of the linear line formed by plotting $(1/T - 1/T_{REF})$ (° K) on the horizontal axis and $\ln(I/I_{REF})$ on the vertical axis. C can be used, along with a reference temperature and reference intensity, to calculate solution temperature when fluorescence is acquired in real-time (see WO2014/058919, already incorporated by reference). In the quantum method, two calibration constants are calculated, one for H(T) calculated before the melting transition, and one for L(T) calculated after the melting transition. Fluorescence data may be plotted according to Equation 3, illustratively with the x-axis being $(1/T - 1/T_{REF})$ and the y-axis being $\ln(I/I_{REF})$. It is understood that this equation may be plotted in other ways, illustratively with the reference value in the numerator on the y-axis, and with $1/T_{REF}-1/T$ for the x-axis. Variations on the way that such data are presented are within the scope of this disclosure.

Figure 2A:
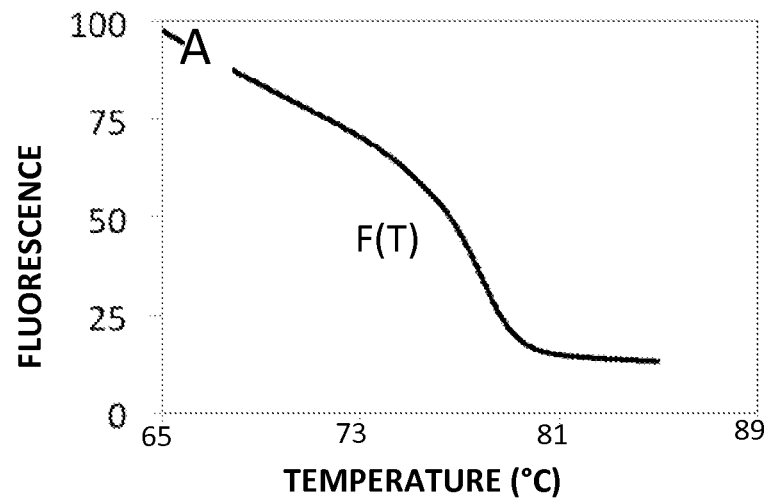
FIGS. 2A-2D show a graphical representation of the quantum method.
Figure 2B:
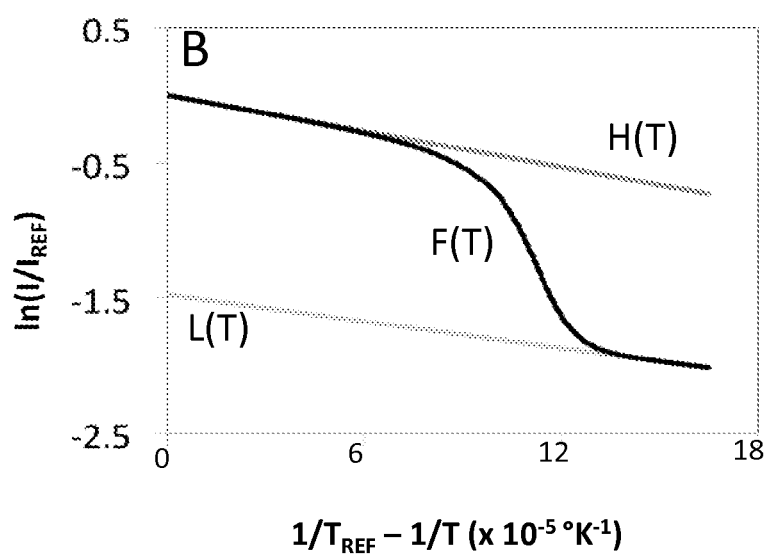
Figure 2C:
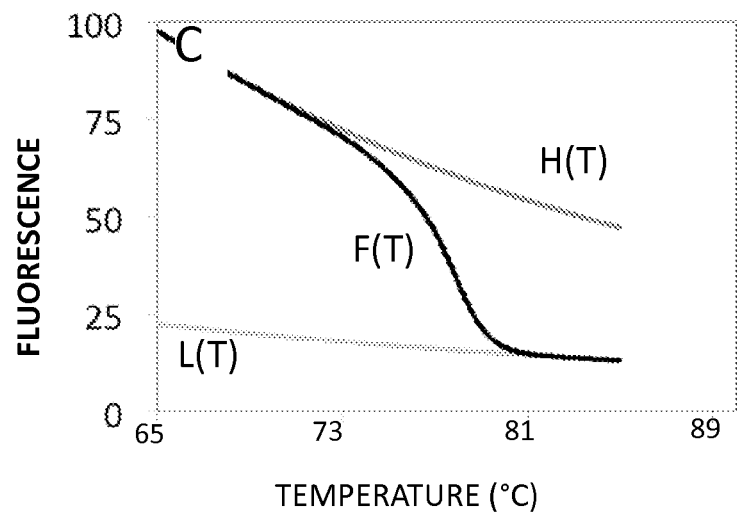

Thus, as seen in FIG. 2B, the quantum method utilizes a reference temperature ($T_{ref}$) and fluorescence ($I_{ref}$), to convert experimental melting curve data (FIG. 2A) to new scales that linearize the effects of temperature on fluorescence outside of the melting transition (FIG. 2B). Reference values are selected from outside of the melting transition. After conversion to ° K, background fluorescence is calculated for the upper (H(T)) and lower (L(T)) bounds as best fit linear equations. Once the equations for H(T) and L(T) are calculated, values are converted back to the original fluorescence and temperature (in ° C.) (see FIG. 2C). The non-linearity of H(T) and L(T) after conversion back to original fluorescence and temperature aids in preventing the early intersection of L(T) and H(T) which may produce algorithm failures in the baseline method (as discussed below).

Figure 2D:
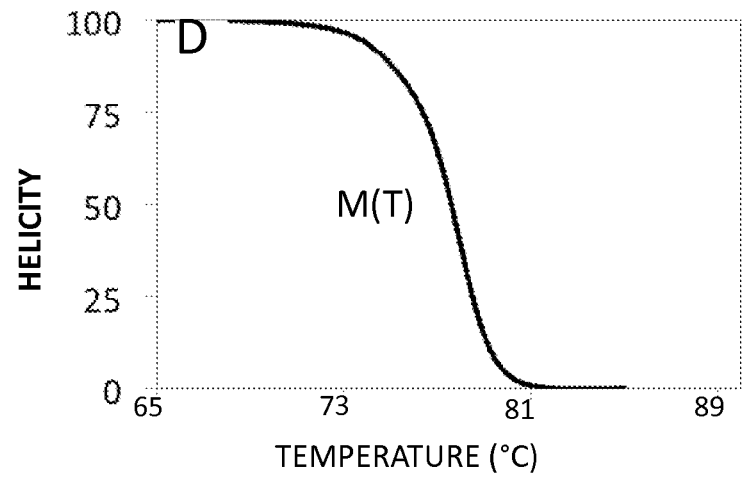

As shown in FIG. 2D, the melting curve then may be proportionally calculated, illustratively using Equation 4, to scale from 0-100% fluorescence.

$$M(T)=F(T)-L(T)/H(T)-L(T) \quad \text{[Equation 4]}$$

where:
M(T)=melting curve
F(T)=fluorescence
H(T)=upper bound
L(T)=lower bound.

Alternatively, other methods may be used for background removal from fluorescent melting data. Illustrative alternate methods include baseline and exponential methods. Descriptions of these algorithms have been previously reported but are briefly included here.

Baseline Method

Figure 3A:
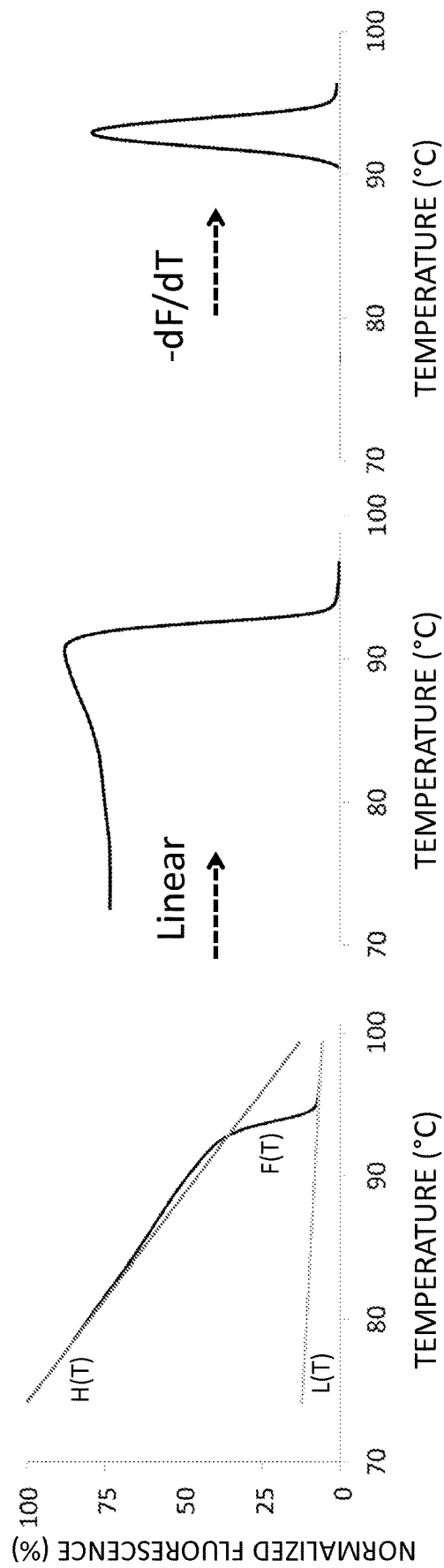
FIGS. 3A-3C show a comparison of background removal algorithms used in fluorescent melting analysis. The baseline (FIG. 3A), quantum (FIG. 3B), and exponential (FIG. 3C) methods are shown. The left panel in each row shows raw experimental melting data F(T) in black, along with calculated background signals (L(T), H(T), and B(T), as appropriate) in grey. After background removal, normalized melting curves (center panel) and negative-derivative plots (right panel) are shown for each method. Melting curves for the baseline and quantum methods are calculated using the equation M(T)=F(T)−L(T)/H(T)−L(T). The exponential method uses the equation M(T)=F(T)−B(T) for melting curve calculation. Differences between the background removal methods are most evident at lower temperatures.

An illustrative baseline method assumes that regions outside of the melting transition (H(T) and L(T)) can be approximated with linear-fits (see FIG. 3A, left panel). The melting curve M(T) is then estimated from the experimental fluorescence data F(T) using Equation 4.

Exponential Method

An illustrative exponential method models experimental fluorescence F(T) as a composite of the melting curve M(T) and an exponentially decaying background signal B(T). Illustratively, B(T) may be calculated by the following equation:

$$y=401849e^{-0.126x} \quad \text{[Equation 5]}$$

Figure 3B:
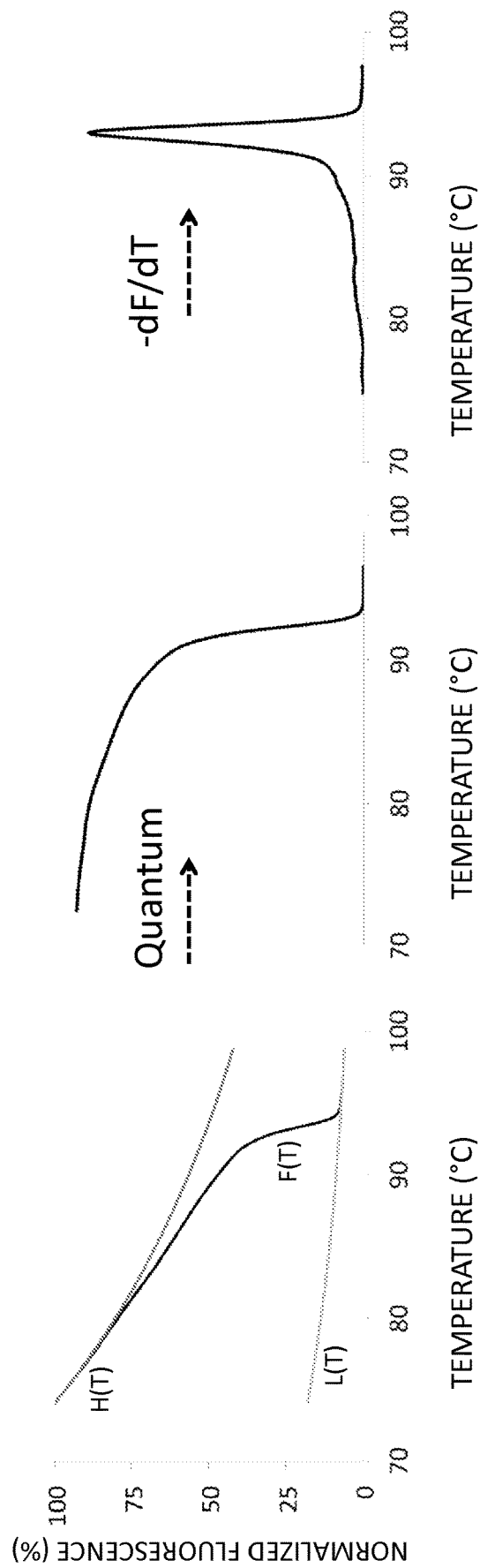
Figure 3C:
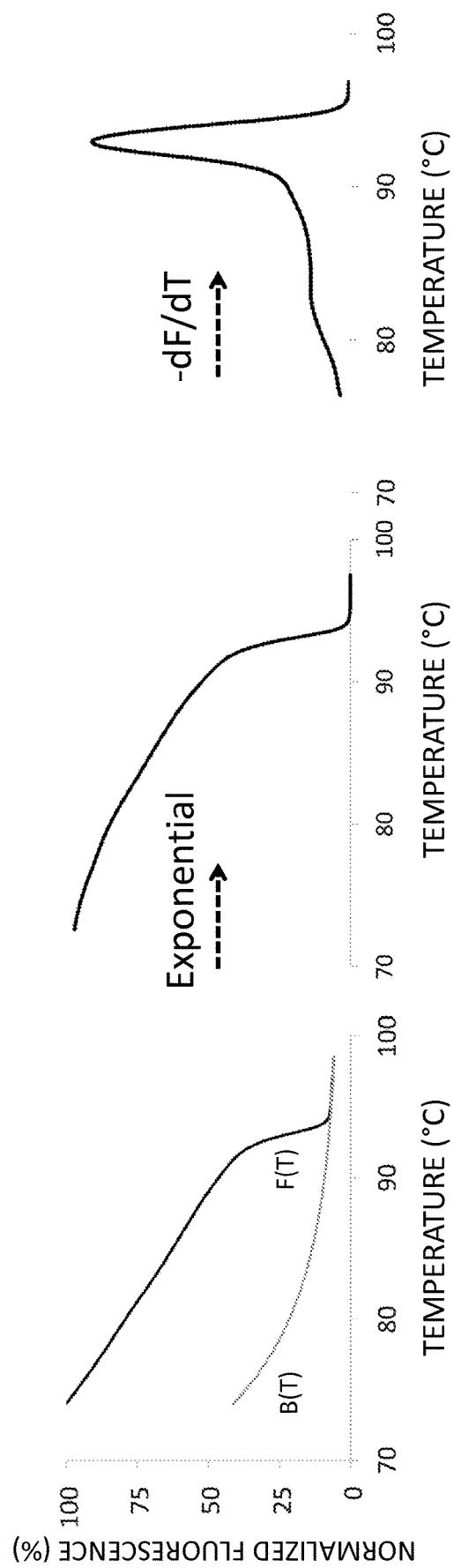

This method involves selecting regions outside of the melting transition where fluorescence is assumed to be comprised of background signal alone. The background signal is then fit to an exponential model, and M(T) calculated by subtracting the resultant background from the experimental fluorescence data (FIG. 3C, left and middle panels) and optionally normalized between 0 and 100% (FIG. 3C, right panel). However, it is understood that Equation 5 is illustrative only and that other equations may be used for the exponential method (see Palais, R.; Wittwer, C. Methods Enzymol. 2009, 454, 323-343 and U.S. Pat. No. 8,068,992, already incorporated by reference).

In the examples discussed below, absorbance and fluorescence melting curves were analyzed using custom software written in LabView (National Instruments), modified to allow comparison between baseline, quantum and exponential algorithms. As recommended in Mergny, J.; Lacroix, L. Oligonucleotides. 2003, 13, 515-537, the baseline method was used for removing background signal from absorbance melting curves, while all three methods were used on fluorescence melting curves (FIGS. 3A-3C). After background removal, all melting curves were normalized for fluorescence intensity, and derivative plots calculated from Savitsky-Golay polynomials to aid in visualizing melting domains and genotypes. On-line software (uMelt$^{SM}$, https://www.dna.utah.edu/umelt/umelt.html) was used to predict melting curves based on recursive, nearest neighbor algorithms that can identify multiple domains.

Absorbance melting curves measured at 260 nm using a UV spectrophotometer were used as a gold standard to judge different methods of background removal from fluorescence melting curves. Linear baseline removal was used for absorbance while baseline, exponential and quantum methods were used with fluorescence. Linear baseline methods often introduced artifacts of increasing fluorescence with temperature (FIG. 3A) or complete failure if the top baseline intersected the bottom baseline before the melting transition (data not shown). Therefore, only exponential and quantum methods are shown in most figures. Absorbance melting curves could only be obtained with synthetic oligonucleotides due to interfering absorbance from the dNTPs with PCR products.

Example 1

Melting of Synthetic Hairpin DNA

Melting of three different types of nucleic acid targets was studied. First, short synthetic hairpins with a 6 bp loop and a 4, 6, 8, or 12 bp stem were examined. The exemplary single-stranded sequences were: 4 bp (5'-GCAGCCCCCCCTGC-3' (SEQ ID NO:1)), 6 bp (5'-TGGCAGCCCCCCCTGCCA-3' (SEQ ID NO:2)), 8 bp (5'-TATGGCAGCCCCCCCTGCCATA-3' (SEQ ID NO:3)), and 12 bp (5'-CGTATATGGCAGCCCCCCCTGC-CATATCAG-3' (SEQ ID NO:4)), wherein bold font denotes the 6 bp loop. The final 100 µL sample volume consisted of 5 µM synthetic DNA, 2 mM $MgCl_2$, and 50 mM Tris-HCl (pH 8.3).

Absorbance was measured at 260 nm using a UV spectrophotometer. In the illustrative examples, changes in DNA helicity across temperature were monitored for using an Ultrospec 2000 (Pharmacia Biotech) at a rate of 1° C./min.

The hairpin loop targets were also measured with fluorescence using dyes that selectively fluoresce in the presence of double stranded DNA. Unless otherwise specified, all fluorescence melting was performed on the HR-1 (BioFire Diagnostics) with 10 µL samples heated at a rate of 0.3° C./s. Melting curves for the short hairpins (15 µM) were acquired in a buffer consisting of 1× LCGreen® Plus, 50 mM Tris-HCl (pH 8.3), 200 µM of each deoxynucleotide triphosphate, 0.5 µg/µL BSA, and 1.6 nl/µL of a KlenTaq™ storage buffer. The $MgCl_2$ concentration was 3 mM for the hairpins. The KlenTaq storage buffer consisted of 50% glycerol (v/v), 50 mM $(NH_4)_2SO_4$, 20 mM Tris-HCl (pH 8.5), 0.1 mM EDTA, 10 mM beta-mercaptoethanol, and 0.5% Triton X-100.

Absorbance and fluorescence melting curves obtained from the synthetic oligonucleotides that formed hairpins are shown in FIGS. 4A and 5A-5C, with relative $T_m$ and peak height data shown in Table 1, below. At all stem lengths, the quantum method, rather than the exponential method, better matched the absorbance data. The exponential method appears to lower $T_m$s. In all stem lengths, the exponential method also produced low temperature bulge artifacts. In some circumstances, such artifacts could be mistaken for additional melting domains. Compared to an absorbance standard, the quantum method raises $T_m$s by 0.7+/−0.4° C.

while the exponential method decreases $T_m$s by 1.5+/−1.2° C. (p=0.01). The peak heights of the quantum method averaged the absorbance data (101+/−14%), while the exponential method tended toward lower peak heights (88+/−20%). Because all melting curves were normalized before the derivative is taken, this value reflects the shape of the melting curve.

TABLE 1

| Stem Length | $\Delta T_m$ from Absorbance (° C.)[a] | | Peak Height (% of Absorbance)[b] | |
|---|---|---|---|---|
| (bp) | Quantum | Exponential | Quantum | Exponential |
| 4 | 1.1 | −2 | 119 | 117 |
| 6 | 0.2 | −2.9 | 88 | 71 |
| 8 | 1 | −1 | 105 | 86 |
| 12 | 0.5 | −0.2 | 92 | 78 |
| Average | 0.7[c] | −1.5[c] | 101 | 88 |
| Standard Deviation | 0.4 | 1.2 | 14 | 20 |

[a]The $\Delta T_m$ from absorbance is the $T_m$ of the fluorescence method (quantum or exponential) minus the $T_m$ of the absorbance data.
[b]The peak height is expressed as a percentage relative to the absorbance data.
[c]p = 0.01 (homoscedastic paired t-test).

Example 2

Melting of Synthetic DNA Using Unlabeled Linear Probes

Also examined was melting of unlabeled linear probes (see U.S. Pat. No. 7,387,887, already incorporated by reference). Synthetic DNA was used to mimic asymmetric PCR where the forward and reverse strands were in 1:5, 1:8, and 1:10 ratios. For the 1:10 strand ratio, the forward strand (5'-TGGCAAGAGGTAACTCAATCACTAGCTTAAAGCACTCTATCCAA-3' (SEQ ID NO:5)) had a final concentration of 0.25 μM, while the final concentration of the reverse strand (5'-TTGGATAGAGTGCTTT AAGCTAGTGATTGAGTTACCTCTTGCCA-3' (SEQ ID NO:6)) was 2.5 μM. The underlined locus denotes the binding site of the probe (5'-CAATCACTAGCTT-3' (SEQ ID NO:7)) at a final concentration of 2.5 μM. For the 1:8 and 1:5 strand ratios, the concentrations of the reverse strand and probe were 2.0 μM with the forward strand was at 0.25 μM (1:8) and 0.4 μM (1:5). The final 200 μL sample also included 2 mM MgCl$_2$ and 50 mM Tris-HCl (pH 8.3).

The third target was a 50 bp synthetic DNA duplex of 50% GC content (Integrated DNA Technologies, Inc.), having the sequence of 5'-TCTGCTCTGCGGCTTTCTGTTTCAGGAATC-CAAGAGCTTTTACTGCTTCG-3' (SEQ ID NO:8) and its perfectly matched complement). The final 100 μL sample included 2 μM synthetic DNA, 1.2 mM MgCl$_2$, and 50 mM Tris-HCl (pH 8.3).

Absorbance was measured as described above. For all unlabeled probe experiments, the sample solution was removed from the test cuvette after the absorbance measurement and diluted 1:10, so that the final 10 μL volume included: 1× LCGreen Plus (BioFire Diagnostics), 55 mM Tris-HCl (pH 8.3), 2.2 mM MgCl$_2$, 200 μM of each deoxynucleotide triphosphate, 0.5 μg/μL BSA, and 1.6 nl/μL of the KlenTaq™ storage buffer described above. Melting curves for the 50 bp duplex (2 μM) were obtained in a buffer consisting of 1× LCGreen Plus, 50 mM Tris-HCl (pH 8.3), 200 μM of each deoxynucleotide triphosphate, 0.5 μg/μL BSA, and 1.6 nl/μL of the KlenTaq™ storage buffer. The MgCl$_2$ concentration was 2 mM for the 50 bp duplex.

Figure 4A:
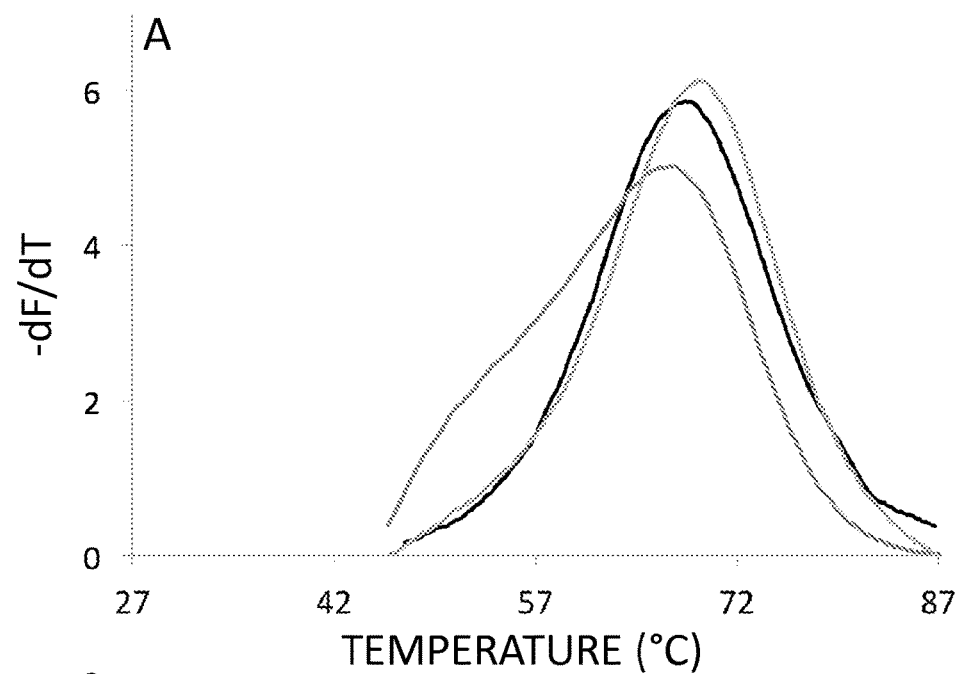
FIGS. 4A-4B show a comparison of different background removal methods using synthetic hairpins and unlabeled probes.
Figure 4B:
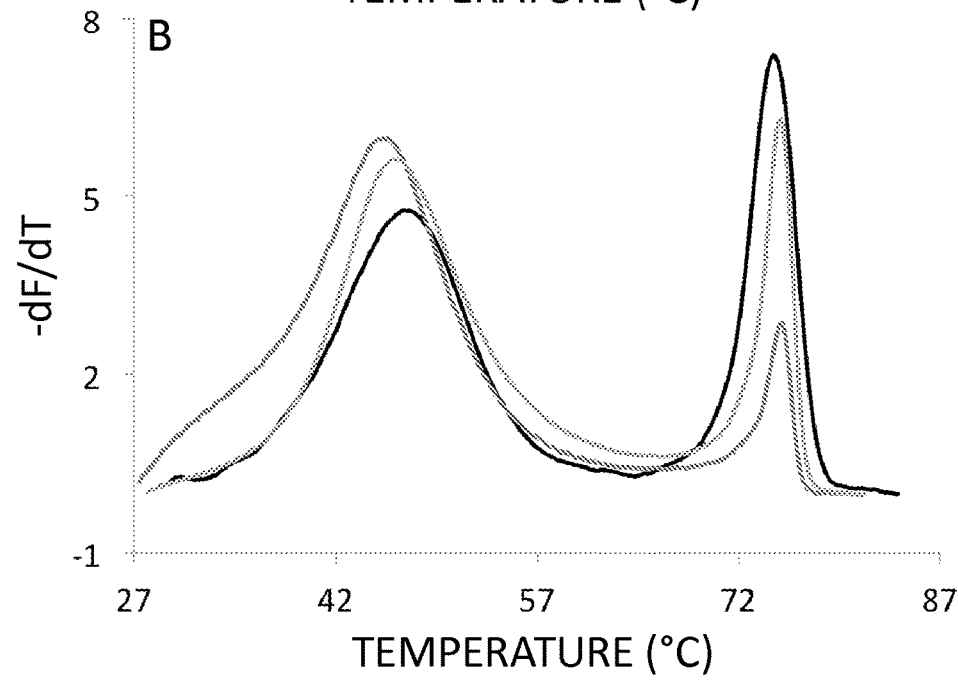
Figure 5A:
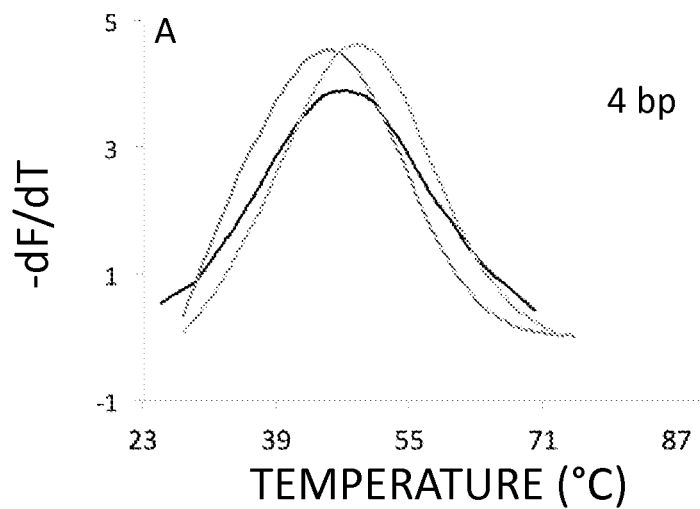
FIGS. 5A-5C show a comparison of synthetic DNA hairpin melting curves monitored by either absorbance or fluorescence. Results from three stem lengths are shown.
Figure 5B:
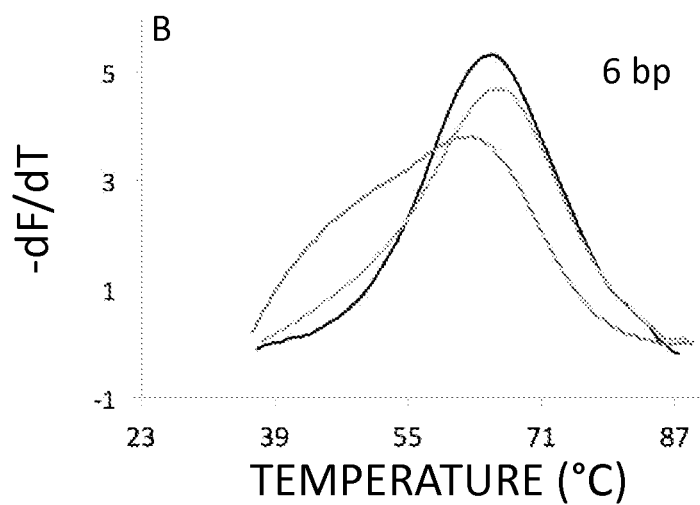
Figure 5C:
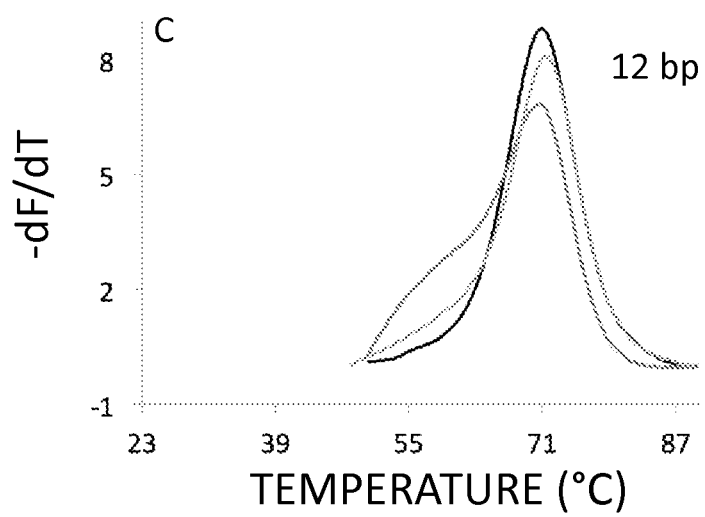
Figure 6A:
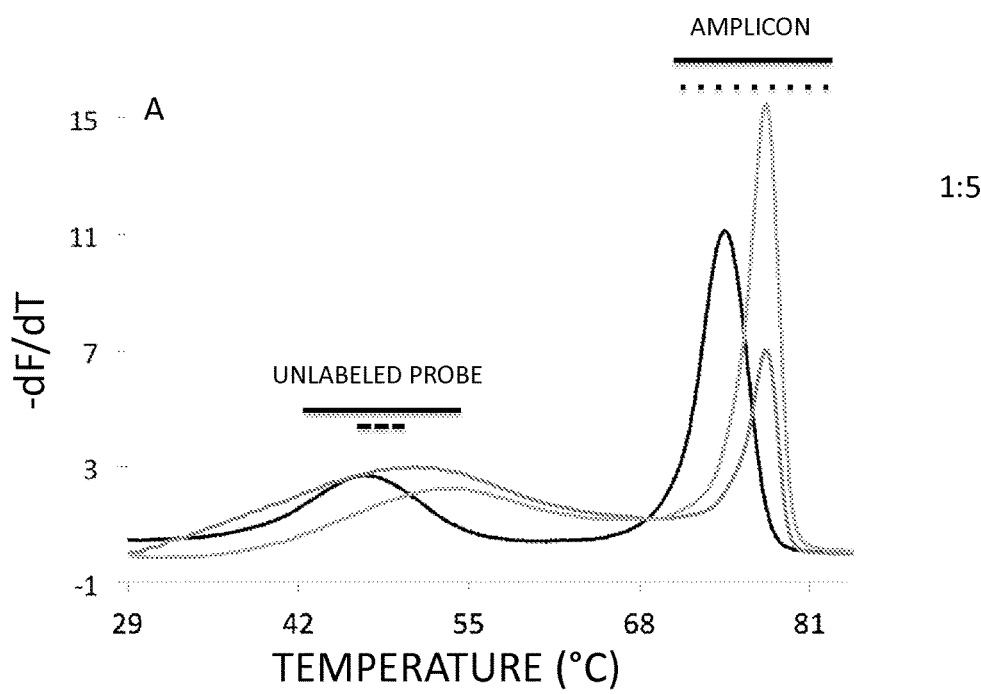
FIGS. 6A-6B show negative-derivative melting plots of complementary synthetic DNA strands (44 bp each) in varying ratios combined with a smaller, sequence-matched unlabeled probe (13 bp). Forward and reverse strand ratios were 1:5 (FIG. 6A) and 1:8 (FIG. 6B) to mimic asymmetric PCR. The 1:10 strand ratio is shown in FIG. 4B. The concentration of the probe was equal to the most abundant strand to mimic unlabeled probe melting analysis. In each panel, the hybridized unlabeled probe region is on the left (at lower temperatuers) and the full-length double stranded amplicon is on the right (at higher temperatures). The baseline method was used for background subtraction of absorbance melting curves (black). Fluorescence melting curves were analyzed using the quantum (light grey) or exponential (dark grey) methods.
Figure 6B:
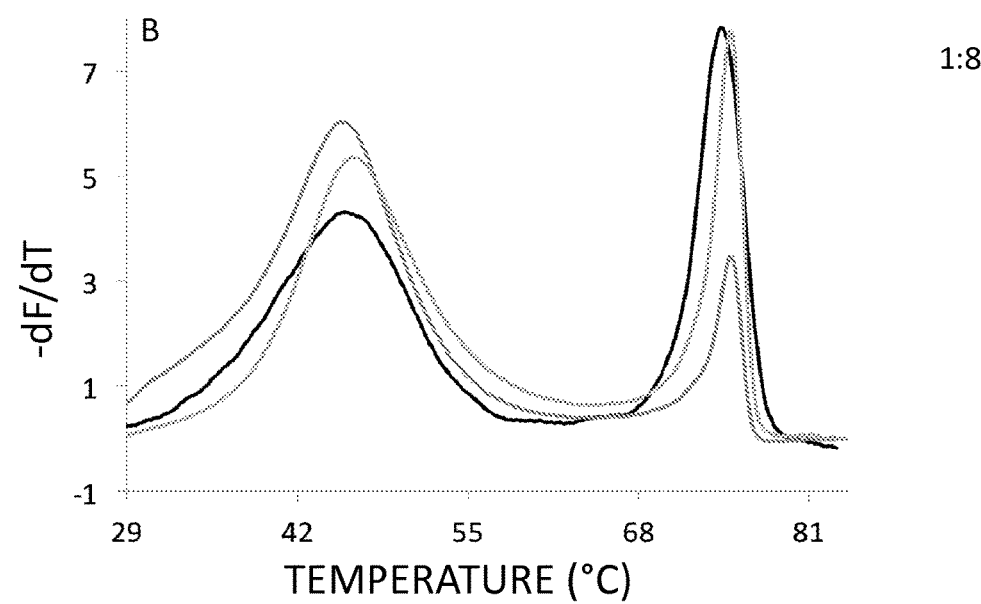

Results for the simulated unlabeled probe analysis are shown in FIGS. 4B and 6A-6B. Unlabeled probe genotyping was simulated with artificial oligonucleotides at strand ratios from 1:5 to 1:10 with relative $T_m$ and peak height data in Table 2, below. The probe melting transition (at lower temperature) is clearly separated from the amplicon melting transition (at higher temperature). The best match to the absorbance data is again the quantum method. In addition to the low temperature bulges seen with the hairpins, the exponential method severely decreases the height of the amplicon peak compared to the quantum method, using absorbance as the gold standard (p=0.03). No significant differences were observed in $T_m$ shifts or for peak heights in the probe region with either method. In summary, when two peaks are present in a melting curve derivative plot, the exponential method appears to decrease the high temperature peaks and increase the low temperature peaks, while the quantum method better matches the peaks heights of the absorbance curves.

TABLE 2

| | $\Delta T_m$ from Absorbance (° C.)[a] | | | | Peak Height (% of Absorbance)[b] | | | |
|---|---|---|---|---|---|---|---|---|
| | Probe Region | | Amplicon Region | | Probe Region | | Amplicon Region | |
| Strand Ratio | Quantum | Exponential | Quantum | Exponential | Quantum | Exponential | Quantum | Exponential |
| 1 to 5 | 7 | 3.5 | 3.1 | 3 | 82 | 108 | 139 | 61 |
| 1 to 8 | 0.5 | −0.2 | 0.7 | 0.7 | 124 | 140 | 99 | 44 |
| 1 to 10 | −0.9 | −1.6 | 0.6 | 0.6 | 118 | 125 | 85 | 38 |
| Average | 2.2 | 0.6 | 1.5 | 1.4 | 108 | 125 | 107[c] | 48[c] |
| Standard Deviation | 4.2 | 2.6 | 1.4 | 1.4 | 22 | 16 | 28 | 12 |

[a]The $\Delta T_m$ from absorbance is the $T_m$ of the fluorescence method (quantum or exponential) minus the $T_m$ of the absorbance data.
[b]The peak height is expressed as a percentage relative to the absorbance data.
[c]p = 0.03 (homoscedastic paired t-test).

Figure 7A:
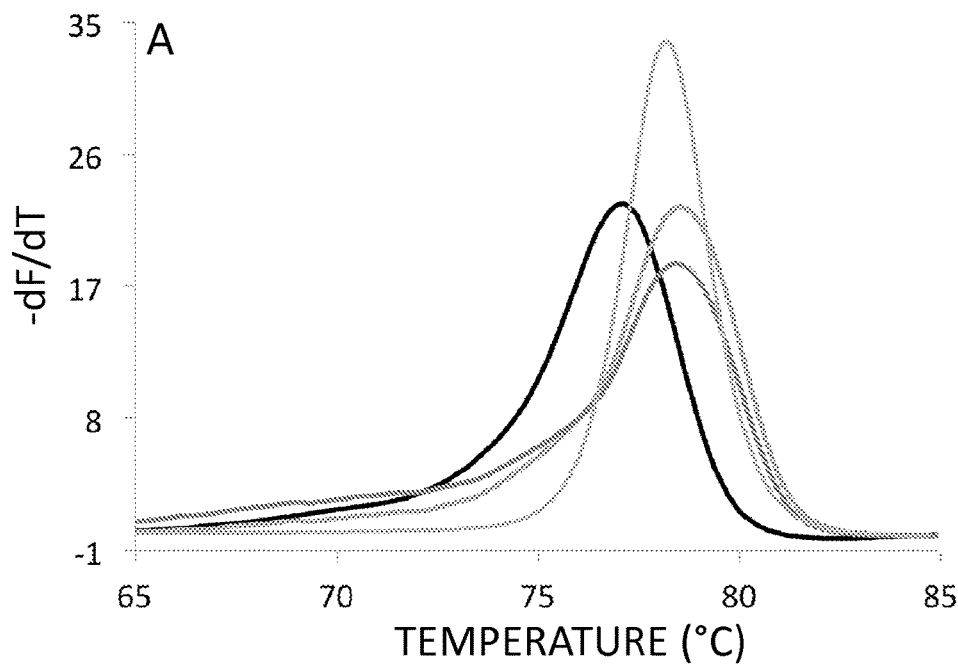
FIGS. 7A-7B show a comparison of different background removal methods on a synthetic 50 bp duplex before (FIG. 7A) and after (FIG. 7B) temperature overlay. The quantum (medium grey) and exponential (dark grey) methods were used to remove background from the fluorescent data acquired at 0.3° C./s. The baseline method was used to normalize absorbance data (black) acquired at 1° C./min. The predicted melting transition (light grey) was generated using the web application uMelt.
Figure 7B:
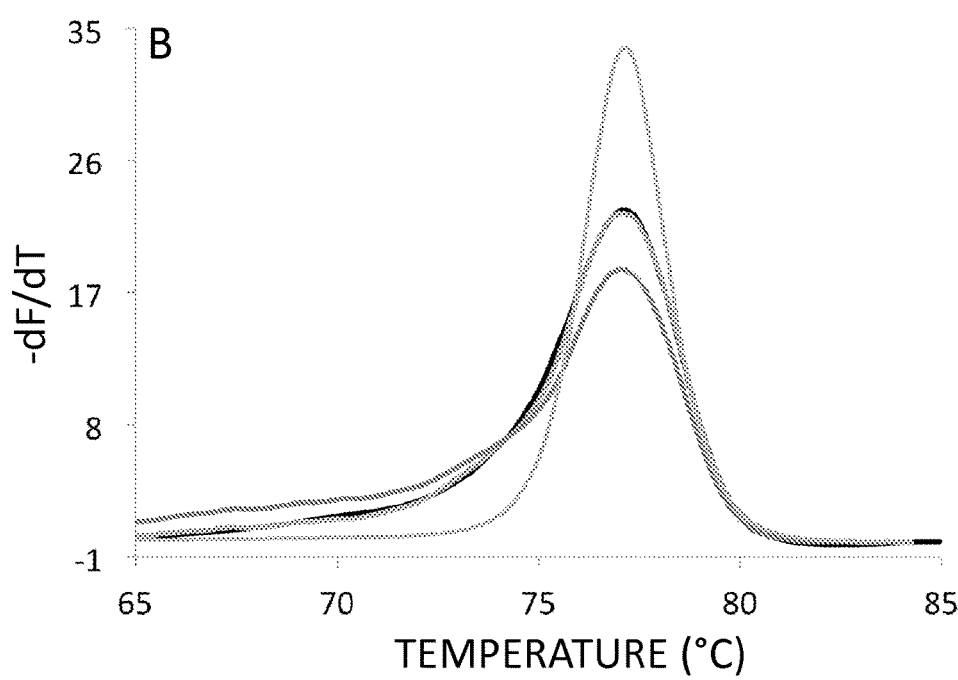

FIGS. 7A-7B compare fluorescence, absorbance, and predicted melting curves for the 50 bp synthetic DNA duplex with and without curve overlay (superimposition along the temperature axis). As shown in FIG. 7A, the $T_m$s of all melting curves are within 1.5° C. of each other. The fluorescence curves have higher $T_m$s than the absorbance curve, possibly reflecting dye stabilization of the 50 bp duplex. When overlaid (FIG. 7B), the shape of the quantum-analyzed fluorescence curve is almost identical to the absorbance curve, strong evidence that helicity is accurately represented by the quantum method. In contrast, the curve shape after exponential analysis is broader and shorter while the predicted melting curve is taller and thinner.

Example 3

Melting of PCR Products Using Fluorescence

Exponential and quantum methods were compared using fluorescence melting data generated after PCR with genotyping assays using unlabeled probes, snapback primers, multiplex short amplicons, and combinations of the above. Genotyping of the factor V Leiden mutation was achieved using unlabeled probes as previously described (see Zhou, L.; Wang, L.; Palais, R.; Pryor, R.; Wittwer, C. Clin. Chem. 2005, 51, 1770-1777). Fluorescent melting curves were generated as described above, but at a melting rate of 0.1° C./s using 5 µL reaction volumes on a LightScanner® 96 sample instrument (BioFire Diagnostics).

Exponential and quantum methods were also compared using symmetric snapback primers (see U.S. Pat. No. 8,399,189, herein incorporated by reference in its entirety) with dilution after PCR. The PCR was performed in 10 µL volumes containing 1× LCGreen Plus, 50 mM Tris-HCl (pH 8.3), 2 mM MgCl$_2$, 200 µM of each deoxynucleotide triphosphate, 0.4 U/µL KlenTaq with antibody, 5 µg/µL BSA, 50 ng DNA per reaction, and 0.5 µM of each primer. The forward primer was 5'-CCtagtgaTGGCAAGAGGTAACTCAATC-3' (SEQ ID NO:9) and the reverse primer was 5'-TTGGATAGAGTGCTTTAAGCT-3' (SEQ ID NO:10). Lowercase lettering denotes the snapback probe, with the underlined uppercase letters denoting the 2-bp mismatch on the 5' end that prevents snapback primer extension from one hairpin. PCR was performed on an S-1000 (Bio-Rad) instrument, with an initial denaturation at 95° C. for 30 s, followed by 10 cycles of a stepdown protocol using 85° C. for 5 s and 73° C.-64° C. for 5 s, ending with 30 cycles of 85° C. for 5 s and 63° C. for 5 s. The reactions were subsequently diluted 10-fold with water, denatured for 2 minutes at 95° C. and allowed to cool down to room temperature. Melting curves (37 to 95° C.) were acquired on a LightScanner at a melting rate of 0.1° C./s.

Illustrative background removal methods were also compared using a duplex small amplicon melting assay with one unlabeled probe, wherein the assay simultaneously detects three missense mutations (p.C282Y, p.H63D, and p.S65C) and one polymorphism (c.T189C) of HFE. The first amplicon is a 40 bp product of HFE encompassing the C282Y mutation amplified with forward primer 5'-TGGGAAGAGCAGAGATATAC-3' (SEQ ID NO:11) and reverse primer 5'-TGGGTGCTCCACCTG-3' (SEQ ID NO:12), both at 0.025 µM final concentrations. The second amplicon is a 78 bp product of HFE containing the lower penetrance mutations (H63D and S65C and the polymorphism T189), amplified with forward primer 5'-TGGGCTACGTGGATGA-3' (SEQ ID NO:13) (0.1 µM) and reverse primer 5'-AAACCCATGGAGTTCGG-3' (SEQ ID NO:14) (0.5 µM). In addition, an unlabeled probe 5'-GCTGTTCGTGTTCTATGATCATGAG<u>GC</u>-P-3' (SEQ ID NO:15) (0.4 µM) was used for genotyping the H63D and T189C variants, with S65C detected by whole amplicon melting. The underline denotes a 2-bp mismatch on the 3' end of the probe. This duplex PCR was performed in 10 µL volumes containing 1× LCGreen Plus, 50 mM Tris (pH 8.3), 500 µg/mL BSA, 3 mM MgCl$_2$, 200 µM of each deoxynucleotide triphosphate, 0.4 U KlenTaq polymerase (Ab Peptides), 64 ng of TaqStart Antibody (eEnzyme), and 5 ng/µL of human genomic DNA. Thermal cycling was performed on a capillary thermal cycler (LightCycler 2.0, Roche). An initial denaturation step at 94° C. for 15 s was followed by 50 cycles of 94° C. for 0 s, 60° C. for 1 s, and 75° C. for 2 s. A final cycle of 94° C. for 0 s and 45° C. for 15 s was also performed. The programmed ramp rates were 20° C./s from denaturation to annealing, 2° C./s from annealing to extension, and 20° C./s from extension to denaturation.

As an example of high-resolution melting containing multiple small amplicons, the results of a quadruplex genotyping assay were also analyzed. Four variants (F5 1601G>A, MTHFR 1286A>C, MTHFR 665C>T, and F2*97G>A) were simultaneously genotyped in a single assay. Information on primer sequences, temperature-correction controls, and PCR conditions have been previously described in detail (see Seipp, M.; Pattison, D.; Durtschi, J.; Jama, M.; Voelkerding, K.; Wittwer, C. Clin. Chem. 2008, 54, 108-115, herein incorporated by reference). Fluorescence melting curves were generated at a melting rate of 0.1° C./s using 10 µL reaction volumes.

Figure 8A:
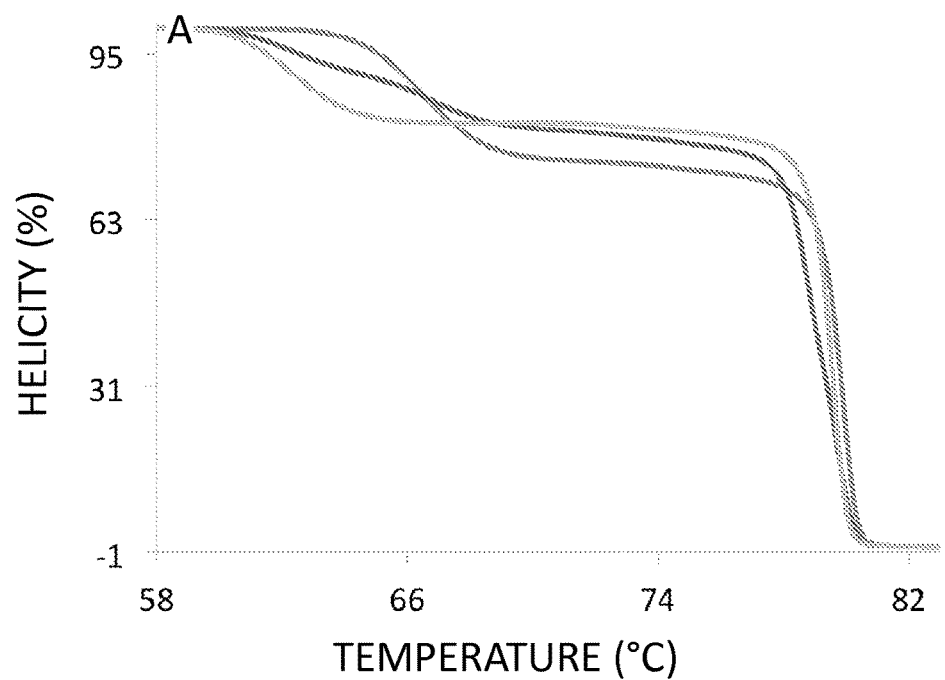
FIGS. 8A-8B show FV genotyping assay with unlabeled probes analyzed using quantum (FIG. 8A) and exponential (FIG. 8B) background removal methods. Wild-type (medium grey), heterozygote (dark grey), and variant (light grey) melting curves are shown.
Figure 8B:
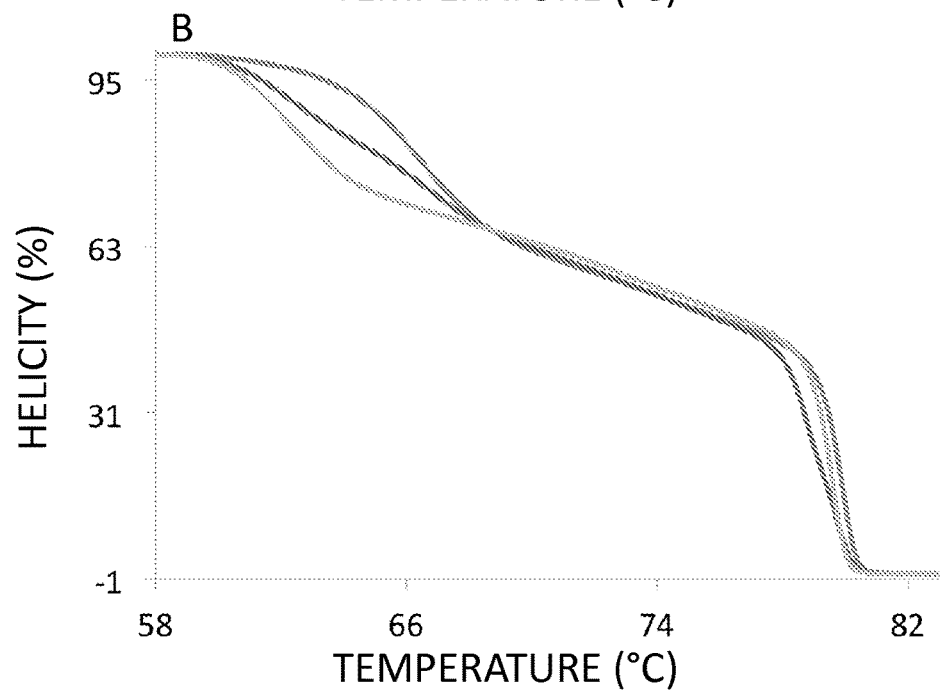

FIGS. 8A-8B show a FV unlabeled probe genotyping assay analyzed by both the quantum (FIG. 8A) and exponential (FIG. 8B) algorithms. With quantum analysis, the region between the unlabeled probe and amplicon is flat, indicating adequate elimination of the temperature effect on fluorescence, while after exponential analysis this region retains a high slope.

Figure 9A:
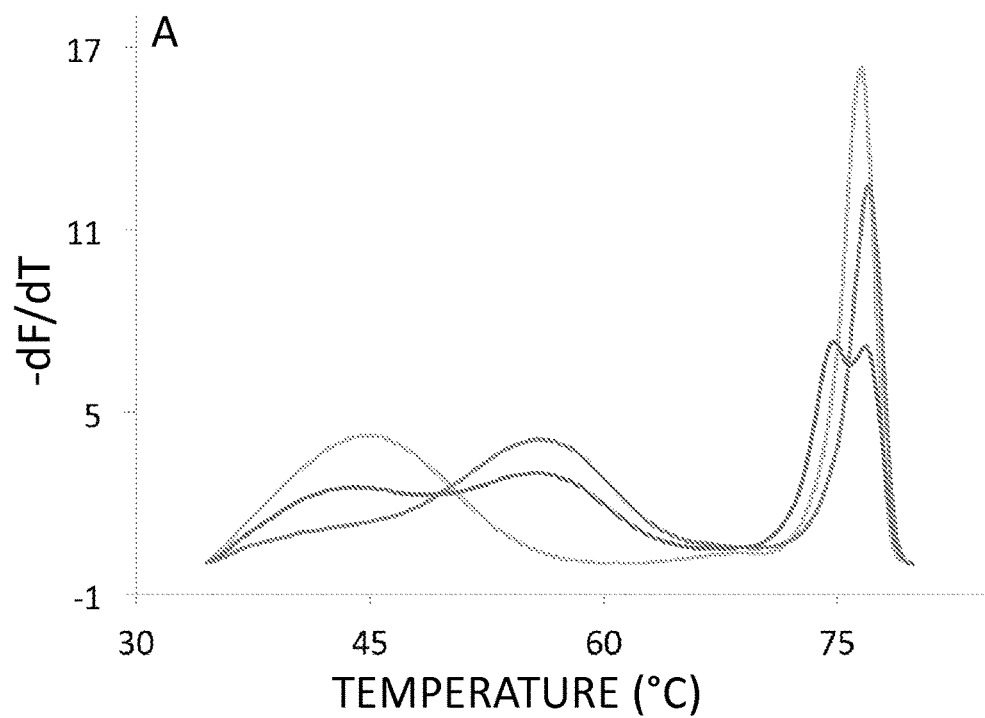
FIGS. 9A-9B show genotyping data using snapback primers analyzed using quantum (FIG. 9A) and exponential (FIG. 9B) methods. Genotypes included wild-type (medium grey), heterozygote (dark grey), and homozygous variant (light grey).
Figure 9B:
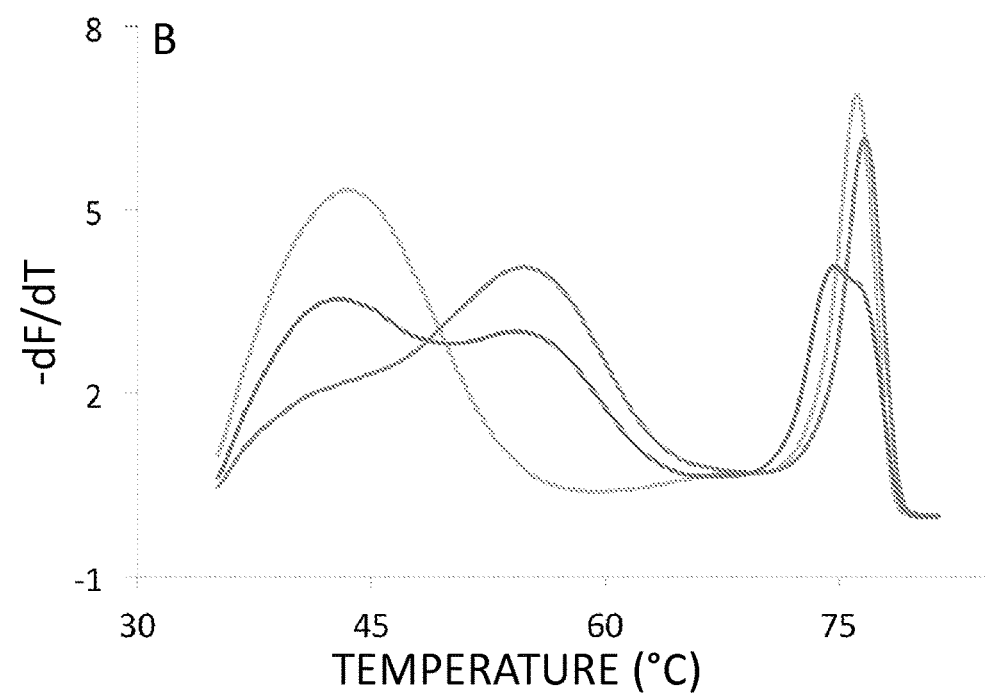

FIGS. 9A-9B show snapback primer single base genotyping using both quantum (FIG. 9A) and exponential (FIG. 9B) algorithms. The hairpin peaks at low temperature are more symmetrical by quantum analysis. Furthermore, exponential analysis produces an apparent low temperature peak in the wild type that potentially could be misinterpreted as heterozygous unless genotype controls are concurrently run and carefully analyzed.

Figure 10A:
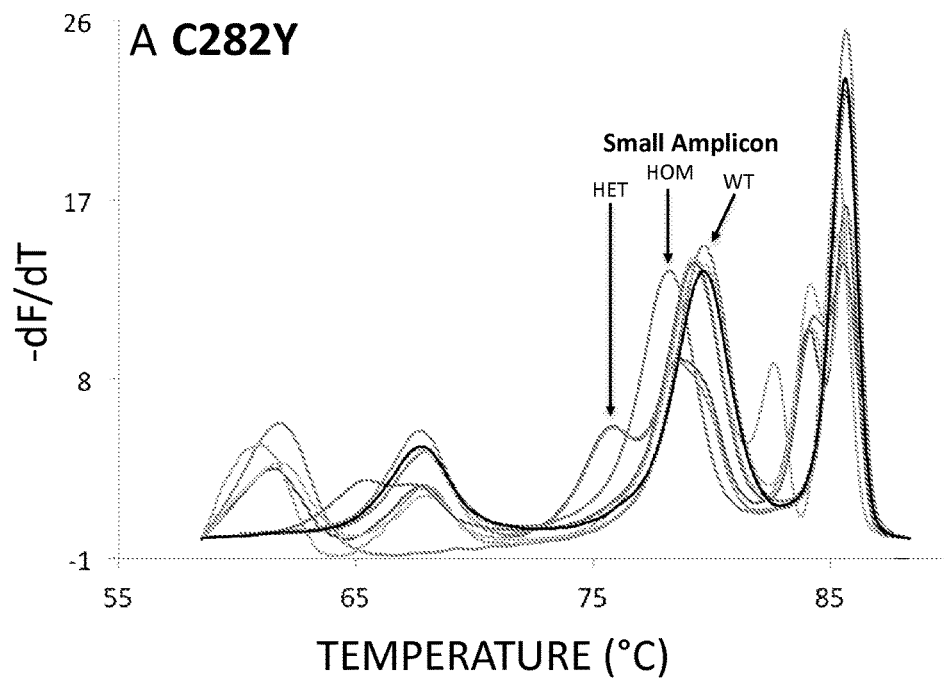
FIGS. 10A-10B show multiplex melting curves showing the simultaneous detection of the p.C282Y, p.H63D, p.S65C and c.T189C variant loci of the HFE gene. Amplicon and probe regions are labeled with bold font and arrows denote signature peaks of different genotypes. The inset schematic shows the full-length amplicon (dashed) with the H63D probe (dot-dashed) in relation to the H63D, S65C, and T189C variants. Data were analyzed using the quantum (FIG. 10A) and exponential (FIG. 10B) methods.
Figure 10B:
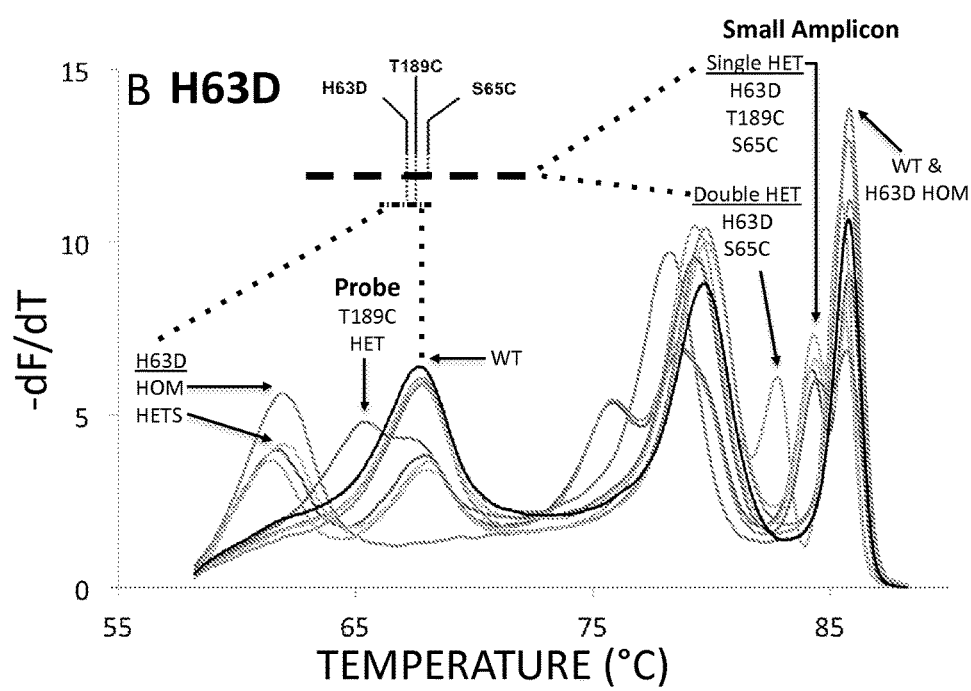
Figure 11A:
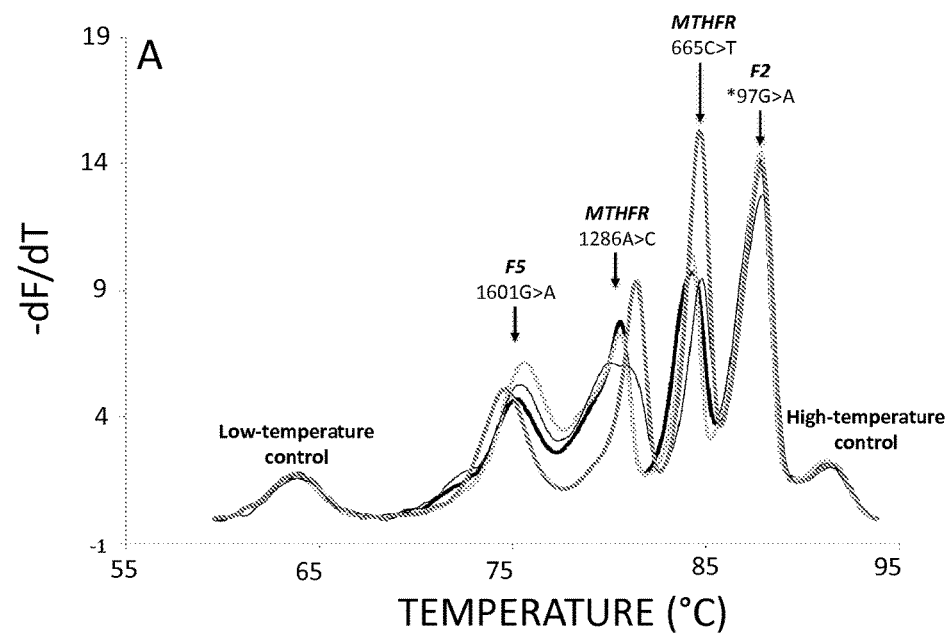
FIGS. 11A-11B show melting curves of the F5, F2, and MTHFR in a quadraplex genotyping assay. The four variants are F5 (c.1601G>A, legacy 1691G>A, rs6025), MTHFR (c.1286A>C, legacy 1298A>C, rs1801131), MTHFR (c.665C>T, legacy 677C>T, rs1801133), and F2 (c.*97G>A, legacy 20210G>A, rs1799963. Data were analyzed using the quantum (FIG. 11A) or exponential (FIG. 11B) methods. Genetic loci and temperature controls are shown in bold font.
Figure 11B:
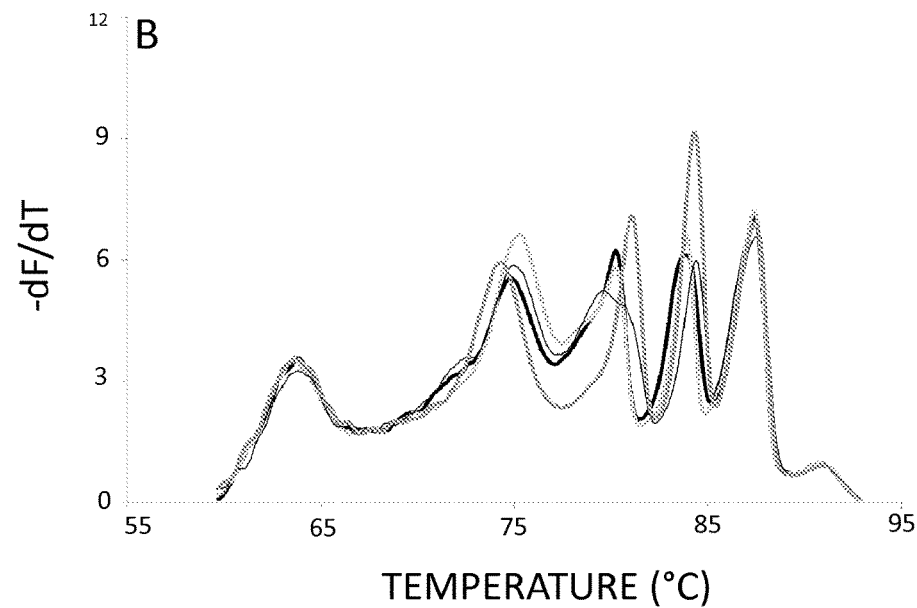

FIGS. 10A-11B and 11A-11B provide examples of more complex genotyping. In FIGS. 10A-10B, a duplex amplification of two small amplicons, one of the amplicons also having an unlabeled probe, are analyzed by quantum (FIG. 10A) and exponential (FIG. 10B) methods. Four single base variants of HFE are genotyped (p.C282Y, p.H63D, p.S65C, and c.T189C). Both quantum and exponential methods provide accurate genotypes, although there is less low temperature artifact with the quantum method. As with the snapback primer analysis above, the exponential method resulted in low temperature shoulders that could potentially lead to erroneous calls. In FIGS. 11A-11B, four single base loci are genotyped by small amplicon melting in the presence of two temperature controls, which can be used for normalization. Similar to HFE, both quantum (FIG. 11A) and exponential (FIG. 11B) methods provide accurate genotypes in this thrombophilia quadruplex assay (F5, F2, and 2 MTHFR variants), although better baselines and reduced low temperature artifacts are observed with the quantum method.

Example 4

Melting System Using Quantum Method

Figure 12:
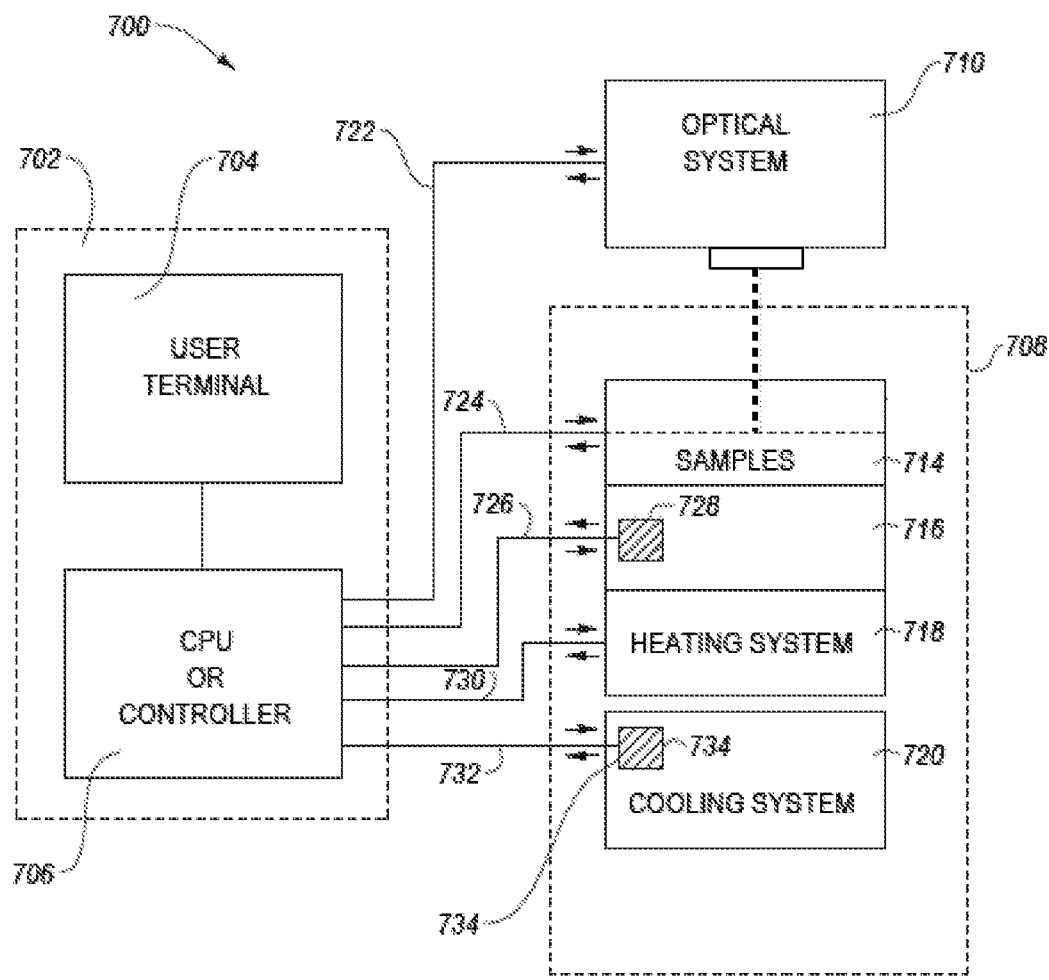
FIG. 12 illustrates a block diagram of an exemplary embodiment of a thermal cycling system in accordance with aspects of the disclosure.

Certain embodiments of the present invention may also involve or include a PCR system configured to generate melting curves using the quantum method. Referring to FIG. 12, a block diagram of an illustrative system 700 that includes control element 702, a thermocycling element 708, and an optical element 710 according to exemplary aspects of the disclosure is shown.

In at least one embodiment, the system may include at least one PCR reaction mixture housed in sample vessel 714. In certain embodiments, the sample vessel 714 may include a PCR reaction mixture configured to permit and/or effect amplification of a template nucleic acid. Certain illustrative embodiments may also include at least one sample block or chamber 716 configured to receive the at least one sample vessel 714. The sample vessel 714 may include one or more individual sample vessels in individual, strip, plate, or other format, and, illustratively, may be provided as or received by a sample block or chamber 716. Optionally, depending on format, a heated cover may be provided to aid in temperature control.

One or more embodiments may also include at least one sample temperature controlling device 718, 720 configured to manipulate and/or regulate the temperature of the sample (s). Such a sample temperature controlling device may be configured to raise, lower, and/or maintain the temperature of the sample(s). In one example, sample controlling device 718 is a heating system and sample controlling device 720 is a cooling system. Illustrative sample temperature controlling devices include (but are not limited to) heating and/or cooling blocks, elements, exchangers, coils, radiators, refrigerators, filaments, Peltier devices, forced air blowers, handlers, vents, distributors, compressors, condensers, water baths, ice baths, flames and/or other combustion or combustible forms of heat, hot packs, cold packs, dry ice, dry ice baths, liquid nitrogen, microwave- and/or other wave-emitting devices, means for cooling, means for heating, means for otherwise manipulating the temperature of a sample, and/or any other suitable device configured to raise, lower, and/or maintain the temperature of the sample(s).

Certain embodiments of the PCR system also include an optical system 710 configured to detect an amount of fluorescence emitted by the sample 714 (or a portion or reagent thereof). Such an optical system 710 may include one or more fluorescent channels, as are known in the art.

At least one embodiment of the PCR system may further include a CPU 706 programmed or configured to operate, control, execute, or otherwise advance the heating system 718 and cooling system 720 to thermal cycle the PCR reaction mixture and to heat the reaction mixture while optical system 710 collects fluorescent signal. CPU 706 may then generate a melting curve, which may be printed, displayed on a screen, or otherwise outputted. Optionally, both a raw melting curve and a melting curve adjusted according to the quantum method may be displayed, or only the adjusted melting curve and/or its derivative is displayed. Optionally the adjusted melting curve or its derivative may be displayed superimposed over other adjusted melting curves or their derivatives from other samples, superimposed over a standard that is run along with the sample, or superimposed over an absorbance melting curve or a predicted melting curve, or any combination thereof. In yet another embodiment, the system 700 generates the melting curve only, using amplification products generated on another instrument or collected from other sources.

Additional examples of illustrative features, components, elements, and or members of illustrative PCR systems and/or thermal cyclers (thermocyclers) are known in the art and/or described above or in U.S. patent application Ser. No. 13/834,056, the entirety of which is herein incorporated by reference.

It is noted that a PCR system according to an embodiment of the present invention may include, incorporate, or otherwise comprise properties, reagents, steps, components, members, and/or elements described in other systems, methods, and/or mixtures disclosed herein.

Thus, using the illustrative system 700 or other known PCR or melting devices, melting curves of synthetic hairpin duplexes (FIGS. 4A and 5A-5C) show that the method of background removal changes the shape, area, and peak height of curves on derivative plots. Predicted $T_m$s using the quantum method were higher than absorbance $T_m$s, while exponential analysis produced lower $T_m$s. Overall curve shape differed between the methods, with the absorbance and quantum data most closely aligning. Absorbance- and quantum-analyzed melting curves show clear, single melting domains, while the exponential method produces a more complex melting transition with a shoulder or secondary melting domain at low temperature. Snapback primers (see U.S. Pat. No. 8,399,189, already incorporated by reference) also result in hairpins after PCR that challenge background removal methods (FIG. 7). The same low temperature distortions occur with the exponential method that can make genotyping difficult.

Genotyping with unlabeled probes results in both amplicon and probe melting transitions (FIGS. 4B, 6A-6B, and 8A-8B). The range of temperatures between the amplicon and the probe in combination with the low probe $T_m$ provides an easy assessment the quality of background removal. As with hairpin data, derivative plots are similarly shaped between absorbance and quantum fluorescence methods. In contrast, a distinct shoulder on the left side of the probe peak is present with the exponential method. In addition, the peak heights of the amplicons are often suppressed with the exponential method, while the quantum method more closely follows absorbance data (Table 2, p=0.03). The same is true when the peak height ratios between the amplicons and probes are considered. That is, exponential background removal augments low temperature signals and attenuates high temperature signals, as compared to absorbance. Potential limitations of the exponential method to remove background accurately are also shown in FIG. 8B, where the fluorescence continues to decrease between the probe and amplicon regions. In contrast, the quantum method (FIG. 8A) results in little change between these regions, as expected.

Absorbance and quantum methods produce nearly identical melting curve shapes for a 50 bp synthetic duplex (FIGS. 7A-7B). In contrast, the exponential method results in a long low-temperature shoulder that correlates with lower peak height. This shoulder is less severe than with hairpins or unlabeled probes, possibly because of the longer duplex. As previously discussed, stabilization of the DNA with dye and/or higher melting rates may explain higher $T_m$s obtained with fluorescence compared to absorbance (see Zhou, L.; Myers, A.; Vandersteen, J.; Wang, L.; Wittwer, C. Clin. Chem. 2004, 50, 1328-1335 and Zhou, L.; Errigo, R.; Lu, H.; Poritz, M.; Seipp, M.; Wittwer, C. Clin. Chem. 2008, 54, 1648-1656). The peak width predicted by uMelt is thinner than the absorbance or fluorescence curves, perhaps because the 50 bp size is at the lower end of the recommended range (50-1000 bp) for the software.

The low temperature distortions and differential amplification that result from exponential background removal are also seen in more complex genotyping assays. Both the HFE (FIG. 10B) and coagulation quadraplex (FIG. 11B) assays show these artifacts, particularly when compared to quantum analysis (FIGS. 10A and 11B). The HFE and quadraplex assays were developed when only the exponential method was available, so it is perhaps not surprising that both exponential and quantum methods resulted in successful genotyping. While the exponential method is a robust method, one might expect that the quantum method with improved background removal would allow even more complex assays to be developed. Also, while it is customary to run standards alongside an unknown, because the quantum method more closely matches absorbance values, it may be possible to genotype without running standards. Illustratively, genotyping may be performed by comparisons to predicted curves or stored absorbance curves.

The use of a temperature-sensitive fluorescent dye to determine solution temperatures has been successful in both flow-field (Lemoine, F.; Antoine, Y.; Wolff, M.; Lebouche, M. Exp. Fluids. 1999, 26, 315-323) and PCR (Sanford, L.; Wittwer, C. Anal Biochem. 2013, 434, 26-33 and Ross, D.; Gaitan, M.; Locascio, L. Anal. Chem. 2001, 73, 4117-4123) applications. The quantum method is based on first principles that describe the excitation of molecules into higher energy states through interaction with electromagnetic radiation. The intensity of fluorescence emission from an organic dye is correlated with its solution concentration (Walker, D. J. Phys. E: Sci. Instrum. 1987, 20, 217-224). For dilute solutions of constant concentration, the general equation is similar to Beer's law (G. Guilbault. Practical Fluorescence, 2nd ed.; Marcel Dekker, Inc.: New York, 1990), and changes in emission intensity may be correlated to changes in temperature. Factors such as the quantum efficiency of the dye, excitation intensity, and molar absorptivity can all impact emission intensity. However, with a stable excitation source, it is the fluorescence quantum yield of the dye that exhibits the strongest sensitivity to temperature, the term "quantum" is used to describe this method of background removal.

In general, fluorescence decreases with increasing temperature due to excited state interactions such as collisional quenching. This physical phenomenon accounts for a majority of background signal in fluorescent melting curves. However, at lower temperatures, it is believed that an additional contributing factor arises: that of the DNA dye binding to highly concentrated primers (Reed, G.; Kent, J.; Wittwer, C. Pharmacogenomics. 2007, 8, 597-608 and Zhou, L.; Errigo, R.; Lu, H.; Portiz, M.; Seipp, M.; Wittwer, C. Clin. Chem. 2008, 54, 1648-1656), and such may require additional modifications to the quantum method presented herein. Accordingly, it is within the scope of this disclosure to augment the quantum method to remove additional artifacts, illustratively those resulting from the amplification mixture.

Accurately removing background signal is an integral and important part of analyzing fluorescent melting curves. While the baseline method is often successful, it typically fails in applications with multiple small amplicons, unlabeled probes and snapback primers. This failure occurs when the lower and upper linear-fits intersect at temperatures below the melting transition, so that the denominator goes to zero and a discontinuity occurs. FIGS. 3A-3C aid in visualizing the differences in background signal as calculated using the baseline, quantum, and exponential methods. While the baseline method does not fail completely in this case, the upper baseline falls below the experimental melting curve, resulting in >100% fluorescence, an upward slope on the melting curve, and negative signals in the derivative plot. FIG. 3B also shows that the quantum method often avoids this failure by allowing non-linear baselines.

Although the baseline curves generated by the quantum method usually do not intersect within the melting region which could result in subsequent failure of the algorithm, rare cases of baseline intersection have been observed on the transformed axis. Without being bound to theory, this may result from low melting signals in relation to primer fluorescence, in combination with selection of the regions that determine the baseline curves. If the baseline curves on the transformed axes intersect in the melting region, then the baselines on the fluorescence vs temperature plots will intersect in the melting region. As a result, the denominator of: $F(T)-L(T)/H(T)-L(T)$ (from Equation 4) will pass through zero and cause a discontinuity or failure from dividing by zero. An example showing the snapback region of an MTHFR amplification is shown in FIGS. 13A-13F.

Figure 13A:
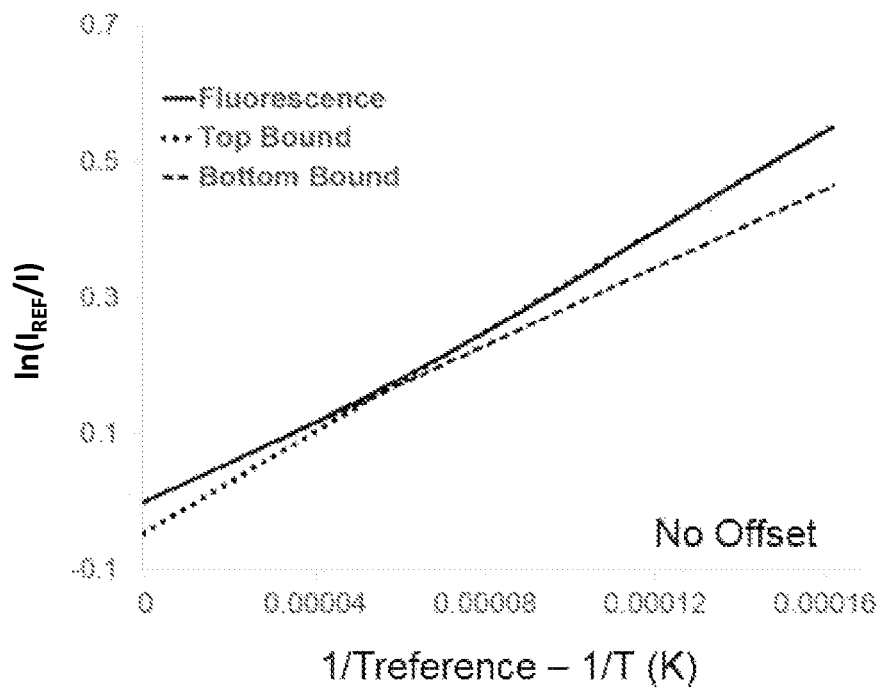
FIGS. 13A-13F show correction for rare cases where baseline intersection have been observed on the transformed axis.
Figure 13B:
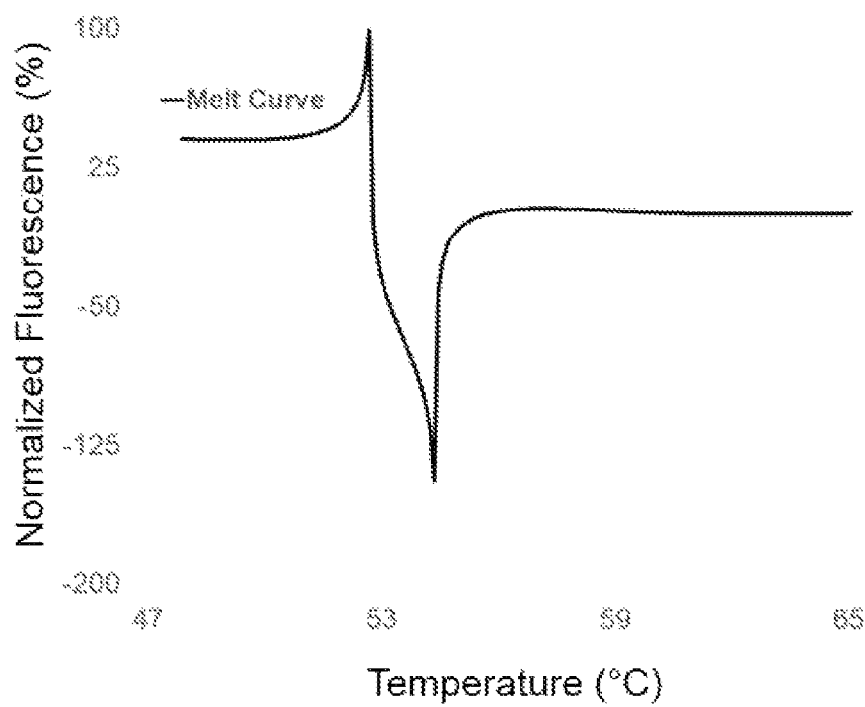
Figure 13C:
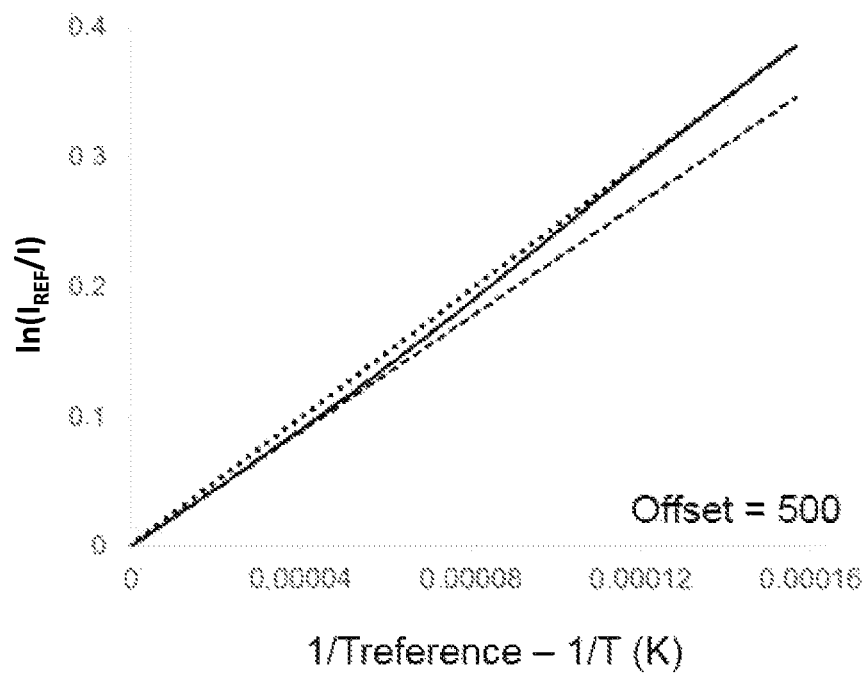
Figure 13D:
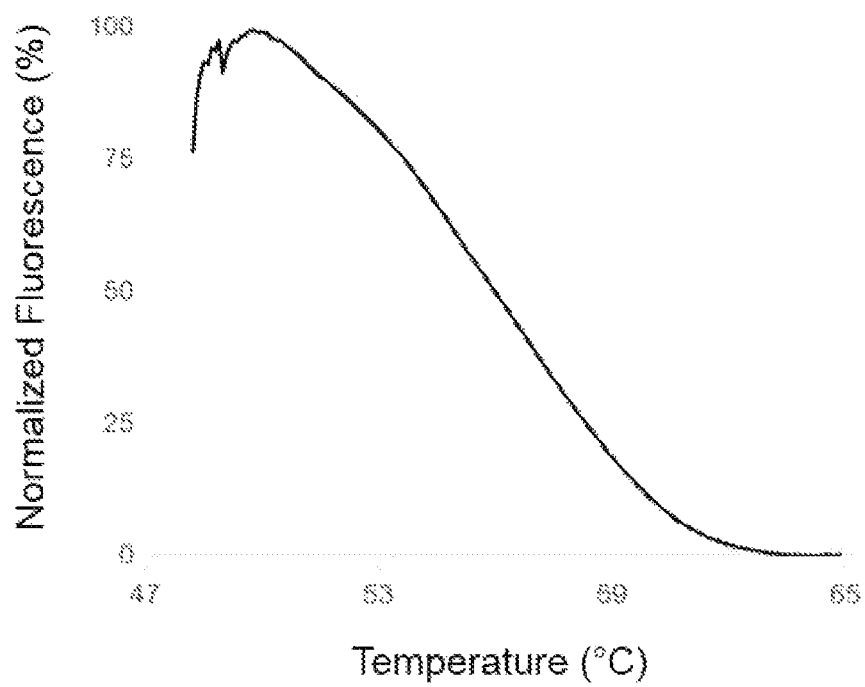
Figure 13E:
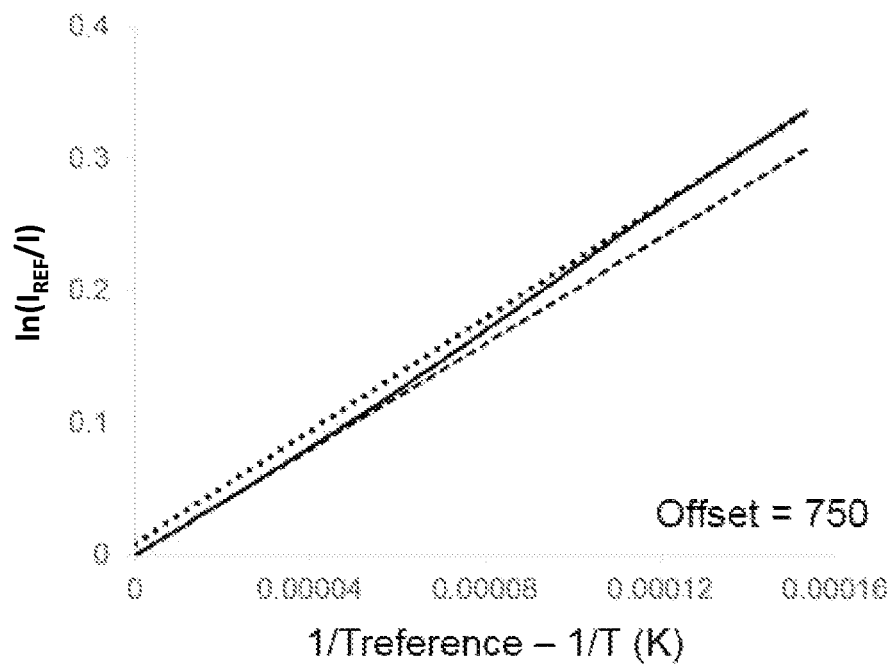
Figure 13F:
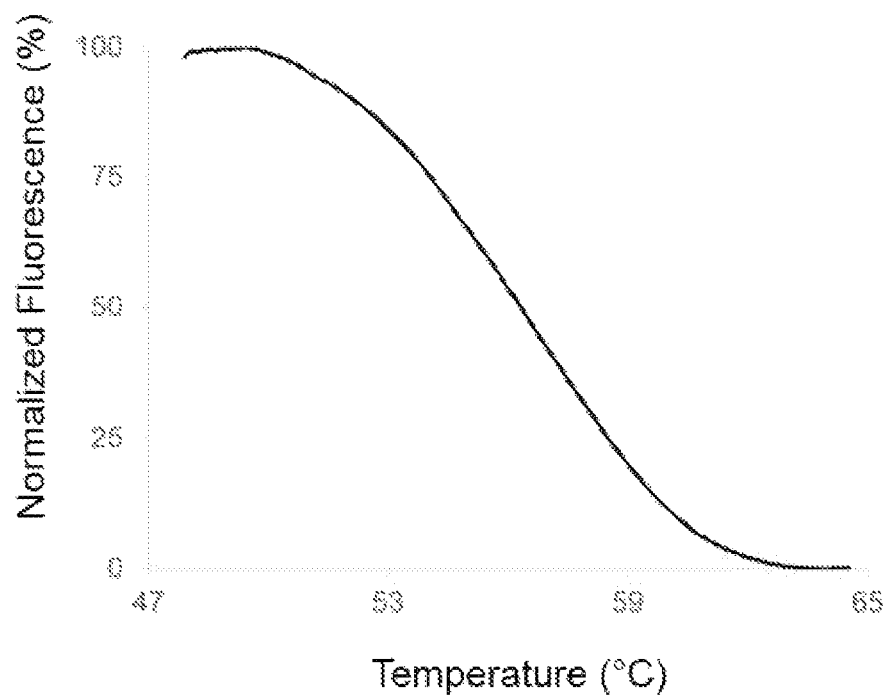

FIGS. 13A-13B labeled, "No offset", demonstrates the rare problem. When plotted on the transformed axis (FIG. 13A), the top and bottom baselines intersect in the region of melting with the experimental curve very close to the top baseline. Because the denominator on the right side of Equation 4 passes through zero at the point of intersection, the melting curve (FIG. 13B) shows discontinuities resulting from very small denominators and a sign change. One solution to this problem is to add a fluorescence offset (addition) to all points on the original melting curve before axis transformation. FIGS. 13C-13F shows offsets of 500 and 750 fluorescence units added to the original data (fluorescence vs temperature) and plotted on the transformed axes (FIGS. 13c and e). Because neither the zero point nor the intensity of fluorescence is absolute, such transformation is justified. As the offset becomes greater, the discontinuities in the final melting curve (FIGS. 13D and 13F), become smaller and finally disappear, resulting in the expected melting curve shape. Adding larger offsets brings $I_{REF}/I$ closer to 1.0 so that $\ln(I_{REF}/I)$ nears zero and does not approach infinity as it would if $I_{REF}/I$ were to approach 0.0 with $I \gg I_{REF}$.

No known background subtraction method completely accounts for all effects presented by the system. The original baseline method has deficiencies at low temperatures. The exponential method almost always functions, but distorts low temperature transitions compared to absorbance, sometimes resulting in a low temperature shoulder. The quantum method is based on first principles and should account for the temperature effect on fluorescence for background removal. However, because of the added fluorescence of primers (unique to each primer set) that result from transitory binding of saturation dyes especially at low temperatures, additional adjustments may be required for accurate presentation of the melting curves. The different methods are summarized in Table 3 below:

TABLE 3

| Method | Artifact | Cause | Solution |
| --- | --- | --- | --- |
| Baseline | Normalized fluorescence >100% as the temperature increases or discontinuity by dividing by zero | Using linear baseline instead of curved baseline. | Exponential or quantum methods |

TABLE 3-continued

| Method | Artifact | Cause | Solution |
|---|---|---|---|
| Exponential | Low temperature peaks or shoulders on derivative plots that do not fit predictions | Exaggeration of low temperature transitions by the exponential method | Quantum method |
| Quantum | Rare discontinuity from dividing by zero or fluorescence >100% | Intersection of high and low baseline within melting region | Increase offset on original melting curve plot |

In one illustrative example, automatic programming to achieve the best offset in the quantum method can be performed. For example, the offset can be incrementally modified until the fluorescence never exceeds 100%. Alternatively, if the concern is baseline curve intersection, the offset can be incrementally increased until the intersection does not occur in the region of melting, and optionally the baseline regions may be modified by adjusting the vertical cursors to define different upper and lower regions for estimation of the baseline curves. In another example, a set amount of fluorescence is added as a standard offset. Other methods of correcting rare failures of the quantum method are also conceived, with non-limiting examples including using a fraction of the total curve fluorescence as the increment or multiplying each curve by a constant in addition to adding an increment to modify the original melting curve before the axes transposition.

The exponential method (FIG. 3C) calculates a single exponentially decaying background signal that removes less background signal at low temperatures compared to the quantum method. On derivative plots, this produces an initial steep slope and higher signal levels at low temperatures. In some instances this artifact is substantial enough so that it may become difficult to discern whether or not low temperature domains are actual duplexes or instead artifacts from the exponential background removal.

All background removal algorithms use regions outside of the melting transition to compute background signal. The region at low temperature necessarily must be about 100% helical (the DNA is double-stranded, with the dye at maximal fluorescence). Thus, the major component of the background signal arises from the effect of temperature on the fluorescence of dye bound to dsDNA, although dye molecules might also interact with the high concentrations of primers present in solution. The final state exhibits about 0% helicity (comprised of denatured single-stranded DNA). In this case, background signal from the fluorescent dye interacting with DNA molecules should be minimal. However, the fluorescent dye remains in solution, so some background of free dye in the presence of denatured DNA exists. The two distinct (and separate) DNA states (100% helicity before the melting transition and 0% after) naturally create two distinct background signals. The benefit of the baseline and quantum methods is that they model the melting curve as a proportional signal that exists between these two DNA states. Thus, the upper fit tracks changes in the background fluorescence of the dsDNA, while the lower fit tracks the background produced by the free dye in solution.

The quantum method results in melting curves that appear to better reflect absorbance curves and the actual percentage of DNA duplex present across the melting transition. Seemingly minute changes can be of diagnostic importance in some high resolution melting. Relevant signals should not be lost in background noise, and background signals must not introduce artifacts that can lead to errors in genotyping and scanning. As advancements in optics and instrumentation proceed forward, more detailed melting curves with higher resolution will be generated, and algorithms for background removal must keep pace to ensure accurate diagnostics.

All references cited herein are incorporated by reference as if fully set forth.

Although the invention has been described in detail with reference to preferred embodiments, variations and modifications exist within the scope and spirit of the invention as described and defined in the following claims.

The invention claimed is:

1. A method for analyzing a melting profile of a nucleic acid sample, comprising measuring the fluorescence of the nucleic acid sample as a function of temperature to produce a raw melting curve having a melting transition, the nucleic acid sample comprising a nucleic acid and a molecule that binds the nucleic acid to form a fluorescently detectable complex, the raw melting curve comprising a background fluorescence signal and a nucleic acid sample signal; and separating the background signal from the nucleic acid sample signal by use of a quantum algorithm to generate a corrected melting curve, the corrected melting curve comprising the nucleic acid sample signal;

wherein separating includes using the following equation:

$$\ln(I/I_{ref}) = C(1/T - 1/T_{ref})$$

where:

$T_{ref}$ is a reference temperature, and $I_{ref}$ is the reference fluorescence intensity of the fluorescent dye at the reference temperature; and wherein the separating step includes rescaling an original x-axis and an original y-axis from the raw melting curve to:

$$x = (1/T - 1/T_{REF})(°K) \text{ and}$$

$$y = \ln(I/I_{REF}).$$

2. A method for analyzing a melting profile of a nucleic acid sample, comprising measuring the fluorescence of the nucleic acid sample as a function of temperature to produce a raw melting curve having a melting transition, the nucleic acid sample comprising a nucleic acid and a molecule that binds the nucleic acid to form a fluorescently detectable complex, the raw melting curve comprising a background fluorescence signal and a nucleic acid sample signal; and separating the background signal from the nucleic acid sample signal by use of a quantum algorithm to generate a corrected melting curve, the corrected melting curve comprising the nucleic acid sample signal;

wherein separating includes using the following equation:

$$\ln(I/I_{ref}) = C(1/T - 1/T_{ref})$$

where:

$T_{ref}$ is a reference temperature, and $I_{ref}$ is the reference fluorescence intensity of the fluorescent dye at the reference temperature; and further comprising adding an offset to the raw melting curve prior to the separating step.

3. A method for analyzing a melting profile of a nucleic acid sample, comprising measuring the fluorescence of the nucleic acid sample as a function of temperature to produce a raw melting curve having a melting transition, the nucleic acid sample comprising a nucleic acid and a molecule that binds the nucleic acid to form a fluorescently detectable complex, the raw melting curve comprising a background fluorescence signal and a nucleic acid sample signal; and separating the background signal from the nucleic acid sample signal by use of a quantum algorithm to generate a corrected melting curve, the corrected melting curve comprising the nucleic acid sample signal;

wherein separating includes using the following equation:

$$\ln(I/I_{ref}) = C(1/T - 1/T_{ref})$$

where:

$T_{ref}$ is a reference temperature, and $I_{ref}$ is the reference fluorescence intensity of the fluorescent dye at the reference temperature; and wherein the nucleic acid sample is genotyped for known sequence variations and scanned for unknown sequence variations.

4. A method for analyzing a melting profile of a nucleic acid sample, comprising measuring the fluorescence of the nucleic acid sample as a function of temperature to produce a raw melting curve having a melting transition, the nucleic acid sample comprising a nucleic acid and a molecule that binds the nucleic acid to form a fluorescently detectable complex, the raw melting curve comprising a background fluorescence signal and a nucleic acid sample signal; and separating the background signal from the nucleic acid sample signal by use of a quantum algorithm to generate a corrected melting curve, the corrected melting curve comprising the nucleic acid sample signal;

$$\ln(I/I_{ref}) = C(1/T - 1/T_{ref})$$

where:

$T_{ref}$ is a reference temperature, and $I_{ref}$ is the reference fluorescence intensity of the fluorescent dye at the reference temperature; and wherein the sample further comprises an unlabeled probe, and the corrected melting curve comprises a melting transition for both a PCR product and an unlabeled probe.

5. A system for analyzing a nucleic acid sample comprising:

a heating system for heating a fluorescently detectable complex while monitoring its fluorescence, the complex comprising a nucleic acid and a fluorescent molecule indicative of double-stranded nucleic acids, the system being adapted to measure and to record sample temperature and sample fluorescence to determine sample fluorescence as a function of sample temperature to produce a melting profile, the melting profile comprising background fluorescence signal and sample fluorescence signal;

a central processing unit (CPU) for performing computer executable instructions; and a memory storage device for storing computer executable instructions that when executed by the CPU cause the CPU to perform a process for analyzing the nucleic acid, wherein the process includes: separating a background fluorescence signal from the melting profile by means of a quantum algorithm to generate a corrected melting curve, the corrected melting curve comprising a sample signal;

wherein separating includes using the following equation:

$$\ln(I/I_{ref}) = C(1/T - 1/T_{ref})$$

where:

$T_{ref}$ is a reference temperature, and $I_{ref}$ is the reference fluorescence intensity of the fluorescent dye at the reference temperature; and wherein the separating includes rescaling an original x-axis and an original y-axis from the raw melting curve to:

$$x=(1/T-1/T_{REF})(° K) \text{ and}$$

$$y=\ln(I/I_{REF}).$$

6. A system for analyzing a nucleic acid sample comprising:
- a heating system for heating a fluorescently detectable complex while monitoring its fluorescence, the complex comprising a nucleic acid and a fluorescent molecule indicative of double-stranded nucleic acids, the system being adapted to measure and to record sample temperature and sample fluorescence to determine sample fluorescence as a function of sample temperature to produce a melting profile, the melting profile comprising background fluorescence signal and sample fluorescence signal;
- a central processing unit (CPU) for performing computer executable instructions; and
- a memory storage device for storing computer executable instructions that when executed by the CPU cause the CPU to perform a process for analyzing the nucleic acid, wherein the process includes: separating a background fluorescence signal from the melting profile by means of a quantum algorithm to generate a corrected melting curve, the corrected melting curve comprising a sample signal;

wherein separating includes using the following equation:

$$\ln(I/I_{ref})=C(1/T-1/T_{ref})$$

where:
$T_{ref}$ is a reference temperature, and
$I_{ref}$ is the reference fluorescence intensity of the fluorescent dye at the reference temperature;
wherein the separating further includes calculating a first line H(T), calculated before the melting transition, and a second line L(T), calculated after the melting transition; and
wherein the separating further includes rescaling the melting profile, H(T), and L(T) to the original x-axis and the original y-axis.

* * * * *